(12) United States Patent
Chin et al.

(10) Patent No.: US 8,460,341 B2
(45) Date of Patent: Jun. 11, 2013

(54) DYNAMIC FACET REPLACEMENT SYSTEM

(75) Inventors: Kingsley Richard Chin, West Palm Beach, FL (US); Christopher A. Chang, Beverly, MA (US); Yani Deros, Phoenix, AZ (US); Matthew Ibarra, Lakewood, CA (US); Thomas Turner, Nashua, NH (US)

(73) Assignee: Spinefrontier Inc, Beverly, MA (US)

( * ) Notice: Subject to any disclaimer, the term of this patent is extended or adjusted under 35 U.S.C. 154(b) by 1030 days.

(21) Appl. No.: 12/146,623

(22) Filed: Jun. 26, 2008

(65) Prior Publication Data

US 2009/0005818 A1  Jan. 1, 2009

Related U.S. Application Data

(63) Continuation-in-part of application No. 11/852,379, filed on Sep. 10, 2007, now abandoned.

(60) Provisional application No. 60/946,422, filed on Jun. 27, 2007.

(51) Int. Cl.
*A61B 17/70* (2006.01)

(52) U.S. Cl.
USPC ........................................ 606/247; 623/17.14

(58) Field of Classification Search
USPC ......... 606/60, 246–249, 256–260; 623/17.11, 623/17.14, 17.16
See application file for complete search history.

(56) References Cited

U.S. PATENT DOCUMENTS

| | | | |
|---|---|---|---|
| 5,092,893 A | 3/1992 | Smith | |
| 6,565,605 B2 | 5/2003 | Goble et al. | |
| 6,579,319 B2 | 6/2003 | Goble et al. | |
| 7,087,084 B2 | 8/2006 | Reiley | |
| 7,147,664 B2 | 12/2006 | Louis et al. | |
| 7,351,261 B2 | 4/2008 | Casey | |
| 7,377,942 B2 | 5/2008 | Berry | |
| 2004/0186475 A1 | 9/2004 | Falahee | |
| 2005/0055096 A1 | 3/2005 | Serham et al. | |
| 2005/0080486 A1 | 4/2005 | Fallin et al. | |
| 2005/0119748 A1* | 6/2005 | Reiley et al. | 623/17.11 |
| 2005/0131409 A1 | 6/2005 | Chervitz et al. | |
| 2005/0131537 A1 | 6/2005 | Hoy et al. | |
| 2005/0131538 A1 | 6/2005 | Chervitz et al. | |
| 2005/0131545 A1 | 6/2005 | Chervitz et al. | |
| 2005/0234551 A1 | 10/2005 | Fallin et al. | |
| 2005/0261770 A1* | 11/2005 | Kuiper et al. | 623/17.11 |

(Continued)

FOREIGN PATENT DOCUMENTS

| | | |
|---|---|---|
| DE | 10135771 A1 | 2/2003 |
| WO | 2007068469 A1 | 6/2007 |
| WO | W02007067547 A2 | 6/2007 |

*Primary Examiner* — Eduardo C Robert
*Assistant Examiner* — Lynnsy Schneider
(74) *Attorney, Agent, or Firm* — AKC Patents LLC; Aliki K. Collins

(57) ABSTRACT

A system for a dynamic facet replacement includes first and second inferior facets, first and second pars and first and second superior facets. The first and second inferior facets are configured to replace left and right natural inferior facets and each facet comprises an articulating surface. The first and second superior facets are configured to replace left and right natural superior facets and each facet comprises an articulating surface. Each of the first and second pars includes first and second articulating surfaces and is configured to articulately connect the first and second articulating surfaces with the first articulating surfaces of the inferior and superior facets, respectively.

16 Claims, 31 Drawing Sheets

U.S. PATENT DOCUMENTS

| | | |
|---|---|---|
| 2005/0267579 A1 | 12/2005 | Reiley et al. |
| 2006/0004449 A1 | 1/2006 | Goble et al. |
| 2006/0004451 A1 | 1/2006 | Goble et al. |
| 2006/0084987 A1* | 4/2006 | Kim ................................ 606/61 |
| 2006/0189983 A1 | 8/2006 | Fallin et al. |
| 2006/0189984 A1 | 8/2006 | Fallin et al. |
| 2006/0217718 A1* | 9/2006 | Chervitz et al. ................ 606/61 |
| 2006/0229609 A1* | 10/2006 | Wang ............................. 606/61 |
| 2006/0265069 A1 | 11/2006 | Goble et al. |
| 2006/0271046 A1* | 11/2006 | Kwak et al. .................... 606/61 |
| 2007/0168035 A1 | 7/2007 | Koske |
| 2007/0198014 A1* | 8/2007 | Graf et al. ...................... 606/61 |
| 2007/0233096 A1 | 10/2007 | Garcia-Bengochea |
| 2007/0233256 A1* | 10/2007 | Ohrt et al. .................. 623/17.11 |
| 2007/0239159 A1 | 10/2007 | Altarac et al. |
| 2008/0015585 A1 | 1/2008 | Berg et al. |
| 2008/0103501 A1 | 5/2008 | Ralph et al. |
| 2008/0103600 A1 | 5/2008 | Casey |
| 2008/0125814 A1 | 5/2008 | Yuan et al. |

* cited by examiner

DYNAMIC FACET REPLACEMENT SYSTEM

CROSS REFERENCE TO RELATED CO-PENDING APPLICATIONS

This application claims the benefit of U.S. provisional application Ser. No. 60/946,422 filed Jun. 27, 2007 and entitled "DYNAMIC FACET REPLACEMENT SYSTEM", the contents of which are expressly incorporated herein by reference.

This application is also a continuation in part of U.S. application Ser. No. 11/852,379 filed on Sep. 10, 2007 and entitled "APPARATUS AND METHOD FOR CONNECTING SPINAL VERTEBRAE" the contents of which are expressly incorporated herein by reference.

FIELD OF THE INVENTION

The present invention relates to a system and method for dynamic facet replacement, and in particular to a facet joint replacement that connects adjacent spinal vertebrae while preserving spinal stability and mobility.

BACKGROUND OF THE INVENTION

The human spine 29 comprises individual vertebrae 30 that interlock with each other to form a spinal column, shown in FIG. 1A. Referring to FIGS. 1B, 1C, 2A, 2B, 3 and 4, each vertebra 30 has a cylindrical bony body (vertebral body) 32, two pedicles 48a, 48b extending from the vertebral body 32, a lamina 47 extending from the pedicles 48a, 48b, three winglike projections (two transverse processes 33, 35 extending from the pedicles 48a, 48b, respectively, and one spinous process 34 extending from the lamina 47), pars interarticularis 36a, 36b, two superior facets 46a, 46b extending from the pedicles 48a, 48b, respectively, and two inferior facets 45a, 45b extending from the lamina 47. The pars interarticularis 36a, 36b connect the superior 46a, 46b and inferior 45a, 45b facets of the vertebra, respectively, on either side of the spinous process 34. The bodies of the vertebrae 32 are stacked one on top of the other and form the strong but flexible spinal column. The spinous process 34, lamina 47, pars interarticularis 36a, 36b, superior facets 46a, 46b, inferior facets 45a, 45b, transverse processes 33, 35, and pedicles 48a, 48b are positioned so that the space they enclose forms a tube, i.e., the spinal canal 37. The spinal canal 37 houses and protects the spinal cord and other neural elements. A fluid filled protective membrane, the dura 38, covers the contents of the spinal canal. The spinal column is flexible enough to allow the body to twist and bend, but sturdy enough to support and protect the spinal cord and the other neural elements. The inferior facets 45a, 45b of one vertebra fit perfectly into the superior facets 46a, 46b of the vertebra below it, thereby forming left and right facet joints 50a, 50b. The facet joints 50a, 50b provide stability and guide motion in the spine. Like the bones that form other joints in the human body, such as the hip, knee, or elbow, the articular surfaces of the facet joints are covered by a layer of smooth cartilage, surrounded by a strong capsule of ligaments, and lubricated by synovial fluid.

The vertebrae 30 are separated and cushioned by thin pads of tough, resilient fiber known as inter-vertebral discs 40. Inter-vertebral discs 40 provide flexibility to the spine and act as shock absorbers during activity. There is a small opening (foramen) 42 between each vertebra 30, through which nerves 44 pass and go to different body parts. When the vertebrae are properly aligned the nerves 44 pass through without a problem. However, when the vertebrae are misaligned or a constriction 15 is formed in the spinal canal, the nerves get compressed 44a and may cause back pain, leg pain or other neurological disorders. Disorders of the spine that may cause misalignment of the vertebrae or constriction of the spinal canal include spinal injuries, infections, tumor formation, herniation of the inter-vertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina 47, i.e., the bony roof of the spinal canal. Discectomy involves removal of the inter-vertebral discs 40. Corpectomy involves removal of the vertebral body 32 as well as the adjacent disc spaces 40. Laminectomy and corpectomy result in central exposure of the dura 38 and its contents. An exposed dura 38 puts the neural elements and spinal cord at risk from direct mechanical injury or scarring from overlying soft tissues. Scarring is considered a major cause for failed back syndrome in which patients continue to have back and leg pain after spinal surgery. Current methods to decrease the risk of developing this syndrome include covering the dura with fat harvested from the patient's subcutaneous tissues or using a synthetic material. However, no material as yet has been used that completely or significantly prevents scarring of the dura and nerve roots after spine surgery in humans.

Furthermore, laminectomy predisposes the patient to instability through the facet joints and may lead to post-laminectomy kyphosis (abnormal forward curvature of the spine), pain, and neurological dysfunction. Therefore the surgeon needs to stabilize the spine after laminectomy procedures and after corpectomy. One spine stabilization method is fusion. Fusion involves the fixation of two or more vertebrae. Fusion works well because it stops pain due to movement of the intervertebral discs 40 or facets 45a, 45b, 46a, 46b, immobilizes the spine, and prevents instability and or deformity of the spine after laminectomy or corpectomy. However, spinal fusion limits spinal mobility. Maintaining spinal mobility may be preferred over fusion in some cases to allow more flexibility of the spine and to decrease the risk of junction problems above and below the level of the fixation due to increased stress.

An arthritic facet joint may also cause back pain (facet arthropathy). Since the majority of the motion along the spine occurs at the facet joints, fusing the diseased facet would often relieve pain but again at a high cost of fusing across at least one spinal segment thus preventing motion and effectively increasing stresses at the adjacent facet joints. Increased stresses predispose facet joints to accelerated arthritis, pain, and instability requiring additional surgery to fuse these levels. This cyclic process results in an overall decreased mobility of the spine. Therefore, it is an attractive alternative to attempt to replace the diseased facet without resorting to fusion, thus avoiding significant limitation in mobility of the spine. The obvious solution would be to replace the opposing surfaces of each facet to preserve motion between the surfaces. However, any efforts to replace the facets at their natural location necessitate destroying the facet capsule and risks producing an unstable joint. Therefore, it is desirable to achieve spine stabilization that preserves mobility, and does not cause tissue scarring or destroy the facet capsule. It is also desirable to be able to implant the stabilization device percutaneously utilizing minimally invasive surgery.

SUMMARY OF THE INVENTION

The present invention relates to a system and method for dynamic facet replacement, and in particular to a facet joint replacement that connects adjacent spinal vertebrae while preserving spinal stability and mobility.

In general in one aspect the invention features a dynamic facet replacement system articulately connecting a first spinal vertebra to an adjacent second spinal vertebra and the second spinal vertebra to an adjacent third spinal vertebra, along the natural facet joints. The facet replacement system includes first and second inferior facet components configured to replace left and right natural inferior facets of the first vertebra, respectively, first and second par components configured to replace left and right natural pars of a second vertebra, respectively, and first and second superior facet components configured to replace left and right natural facets of a third vertebra, respectively. Each of the inferior and superior facet components comprises a facet articulating surface and each of the par components comprises first and second par articulating surfaces. The first and second par components are shaped and dimensioned to be inserted between the first and second inferior and superior facet components, respectively, and to articulately connect the first and second inferior facet components to the first and second superior facet components, respectively, by connecting the first and second par articulating surfaces to the facet articulating surfaces of the inferior and superior facet components, respectively.

Implementations of this aspect of the invention may include one or more of the following features. The connection of the par components to the inferior and superior facet components comprises a surface-to-surface articulation mechanism or a constrained articulation mechanism. The constrained articulation mechanism comprises a male articulation component engaging a female articulation component. Each of the inferior facet components comprises a first extension member protruding from the inferior facet articulating surface and each of the par components comprises a first groove formed in the first par articulating surface and wherein the first groove is shaped and dimensioned to receive the first extension member and thereby to articulately connect the inferior facet component to the par component. Each of the par components further comprises a second extension member protruding from the second par articulating surface and wherein the superior facet component comprises a second groove formed in the superior facet articulating surface and wherein the second groove is shaped and dimensioned to receive the second extension member and thereby to articulately connect the superior facet component to the par component. Each of the inferior facet components comprises an elongated curved body and the body comprises a first cylindrical shaped end, configured to be attached to a location of the first vertebra and a second cylindrical shaped end comprising the inferior facet articulating surface. In each of the inferior facet components, the first cylindrically shaped end's axis is oriented perpendicular to the second cylindrical shaped end's axis. Each of the par components comprises an elongated curved body and the body comprises a first cylindrical shaped end, configured to be attached to a location of the second vertebra, a second cylindrical shaped end comprising the second par articulating surface, and wherein the first cylindrically shaped end further comprises a wing extension comprising the first par articulating surface. In each of the par components the first cylindrically shaped end's axis is oriented perpendicular to the second cylindrical shaped end's axis. Each of the superior facet components comprises a cylindrically shaped end, configured to be attached to a location of the third vertebra and wherein the cylindrically shaped end further comprises a wing extension comprising the superior facet articulating surface. Any of the cylindrically shaped ends is attached to the vertebral locations via a poly-axial screw. Any of the vertebral locations comprise one of a pedicle, transverse processes, facets, pars interarticularis, intervertebral disc, lamina, or vertebral body. The dynamic facet replacement system comprises at least one of metal, plastic, ceramic, bone, polymers, composites, absorbable material, biodegradable material, or combinations thereof. The vertebras comprise one of cervical, thoracic, lumbar or sacrum vertebras. The male articulation component comprises an extension member and the female articulation member comprises a slot shaped and dimensioned to receive the extension member. The constrained articulation mechanism further comprises a locking member configured to fit over the slot and to lock the extension member within the slot.

In general in one aspect the invention features a method for articulately connecting a first spinal vertebra to an adjacent second spinal vertebra and the second spinal vertebra to an adjacent third spinal vertebra, along the natural facet joints. The method includes providing first and second inferior facet components configured to replace left and right natural inferior facets of a first vertebra, respectively, and attaching the first and second inferior facet components to first and second locations of the first vertebra, respectively. Each of the inferior facet components comprises an articulating surface. Next, providing first and second par components configured to replace left and right natural pars of a second vertebra, respectively, and attaching the first and second par components to first and second locations of the second vertebra, respectively. Each of the par components comprises first and second par articulating surfaces. Next, providing first and second superior facet components configured to replace left and right natural facets of a third vertebra, respectively, and attaching the first and second superior facet components to first and second locations of the third vertebra, respectively. Each of the superior facet components comprises an articulating surface. Finally, articulately connecting the first and second par articulating surfaces to the articulating surfaces of the inferior and superior facet components, respectively. The connection of the par components to the inferior and superior facet components comprises a constrained articulation mechanism and the constrained articulation mechanism comprises a male articulation component engaging a female articulation component. The male articulation component comprises an extension member and the female articulation member comprises a slot shaped and dimensioned to receive the extension member, and wherein the constrained articulation mechanism further comprises a locking member configured to fit over the slot and to lock the extension member within the slot.

Among the advantages of this invention may be one or more of the following. The implantable spinal stabilization device stabilizes the spine along the facet joints, while allowing the patient to retain spinal flexibility by preserving motion between adjacent vertebras. This spinal stabilization device may be implanted using minimally invasive surgery along lines left and right of the midline of the spinal column. The spinal stabilization device may be used for the treatment of a multitude of spinal disorders including facet arthritis and spinal stenosis. The implantable device has a compact structure and low profile. The implant can be inserted percutaneously along the sides of the spine without the need to make a large midline incision and stripping the erector spinal muscles laterally. There is no need to remove the posterior elements of the vertebras such as the spinous processes and lamina.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

The present invention relates to a system and method for dynamic facet replacement, and in particular to a facet joint replacement that connects adjacent spinal vertebrae while preserving spinal stability and mobility.

Figure 1A:
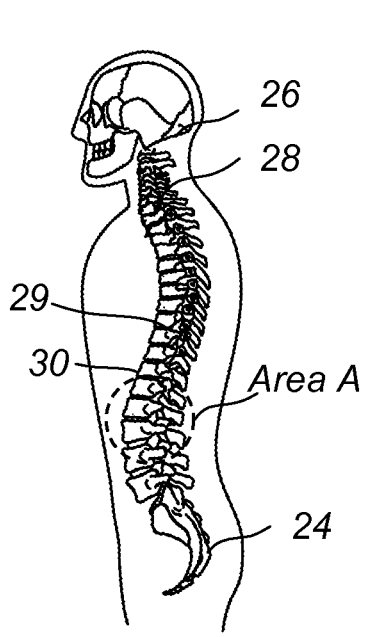
FIG. 1A is a side view of the human spinal column.
Figure 1B:
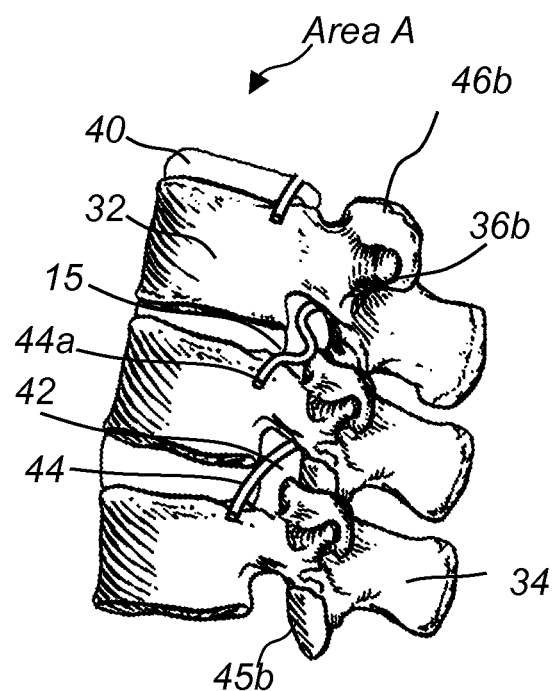
FIG. 1B is an enlarged view of area A of FIG. 1A.
Figure 1C:
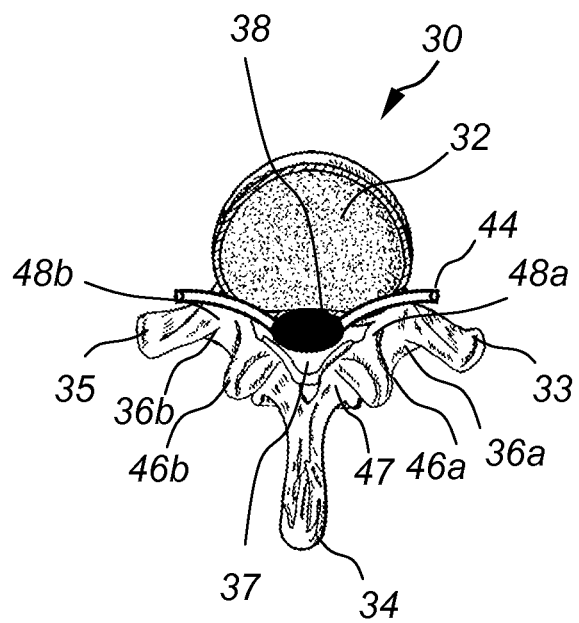
FIG. 1C is an axial cross-sectional view of a lumbar vertebra.
Figure 2A:
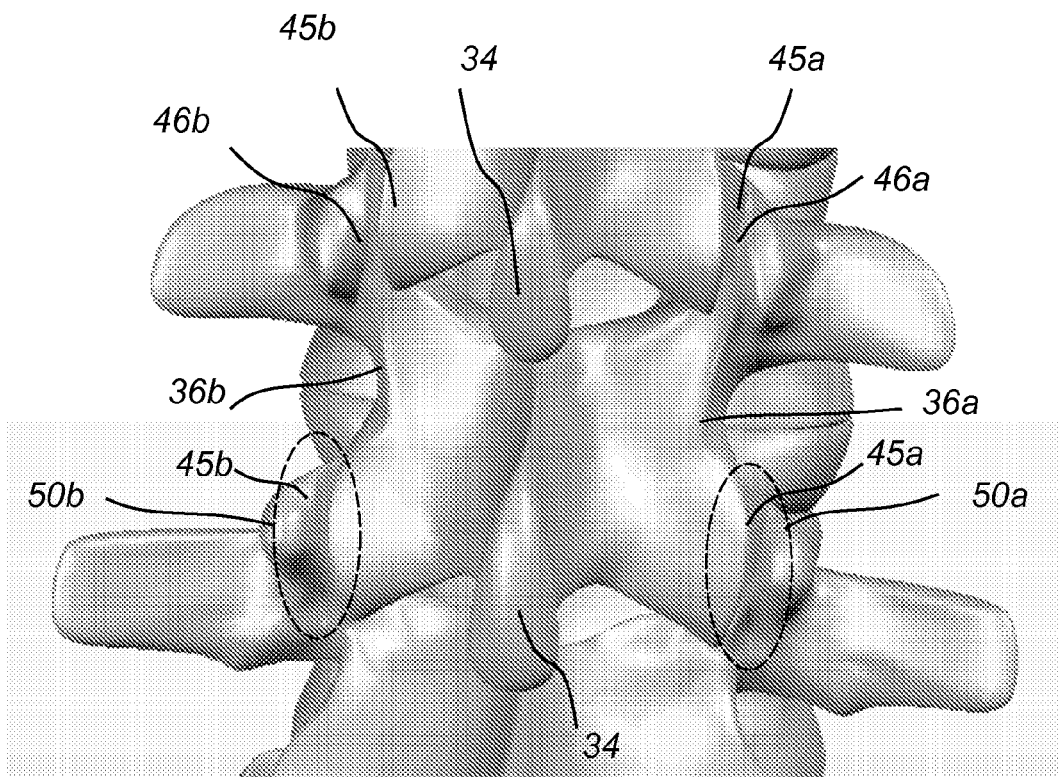
FIG. 2A illustrates the facet joints of two adjacent vertebras.
Figure 2B:
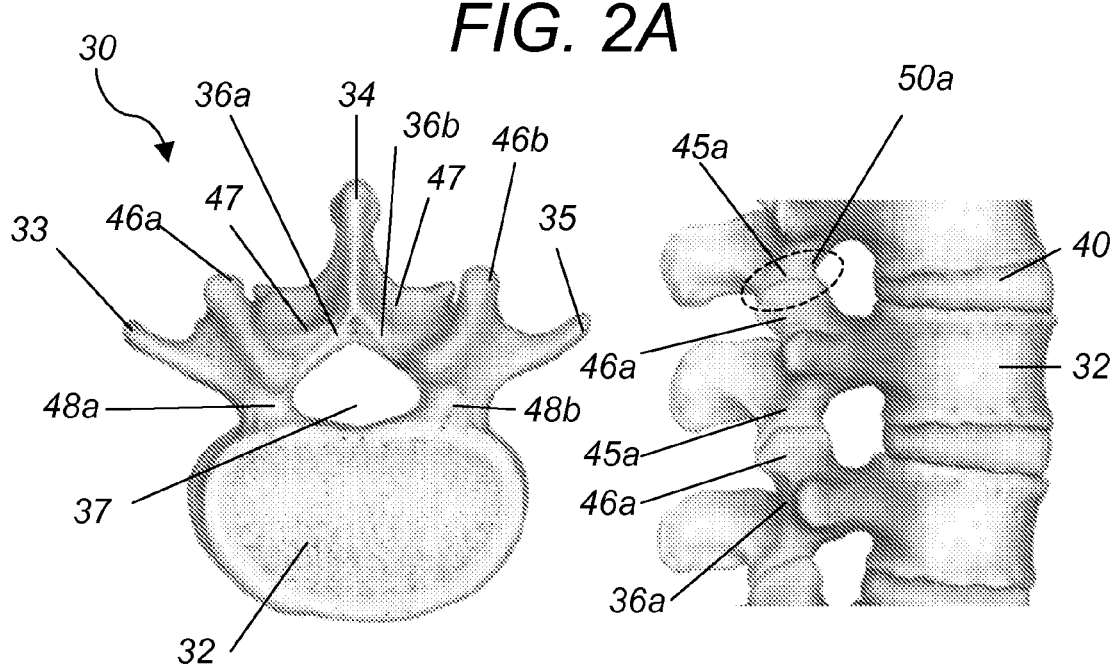
FIG. 2B illustrates another axial cross-sectional view of a lumbar vertebra and a side view of adjacent lumbar vertebras.
Figure 3:
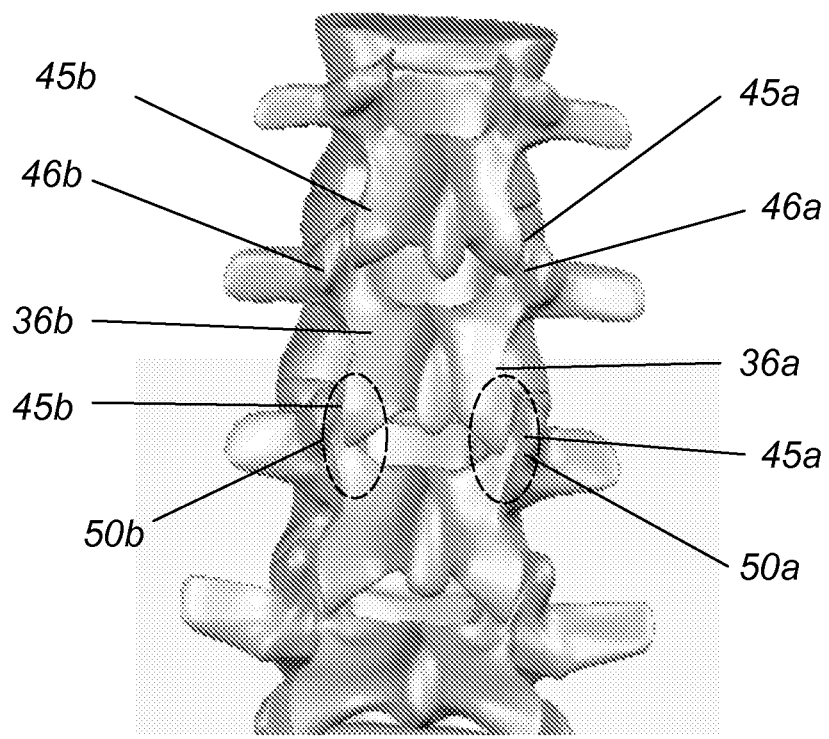
FIG. 3 is a front (posterior) perspective view of the lumbar section of the human spinal column.
Figure 4:
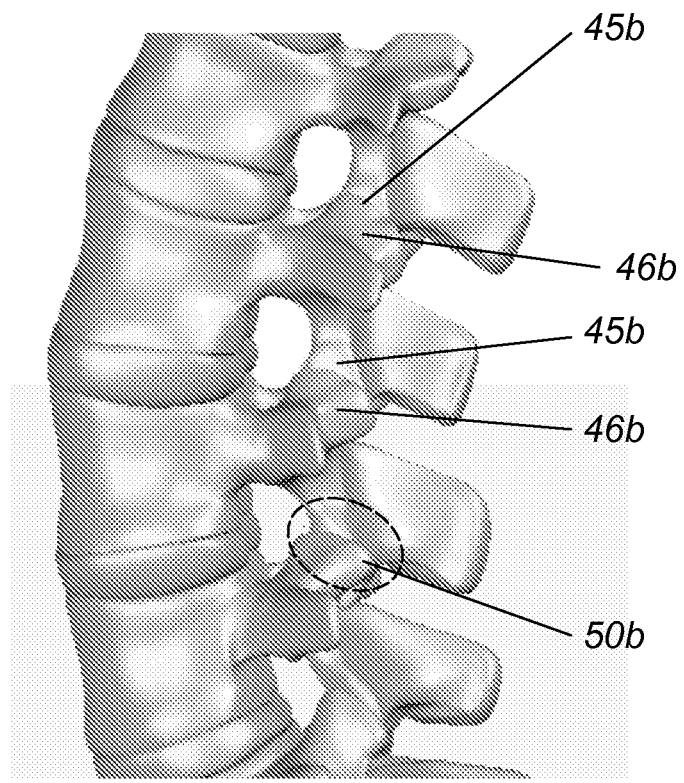
FIG. 4 is a side view of the lumbar section of FIG. 3.
Figure 5:
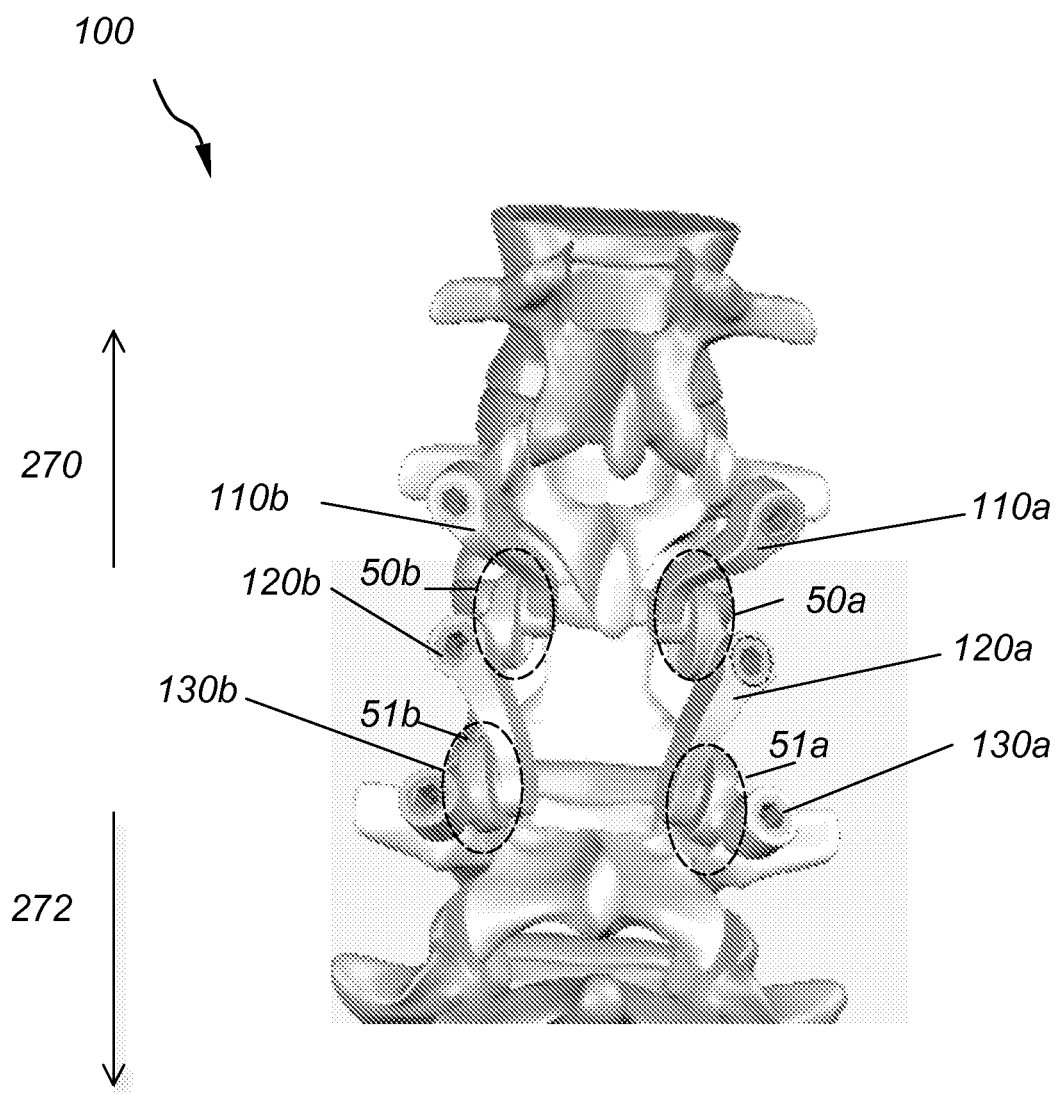
FIG. 5 is a front (posterior) perspective view of an embodiment of the dynamic facet replacement system.
Figure 6:
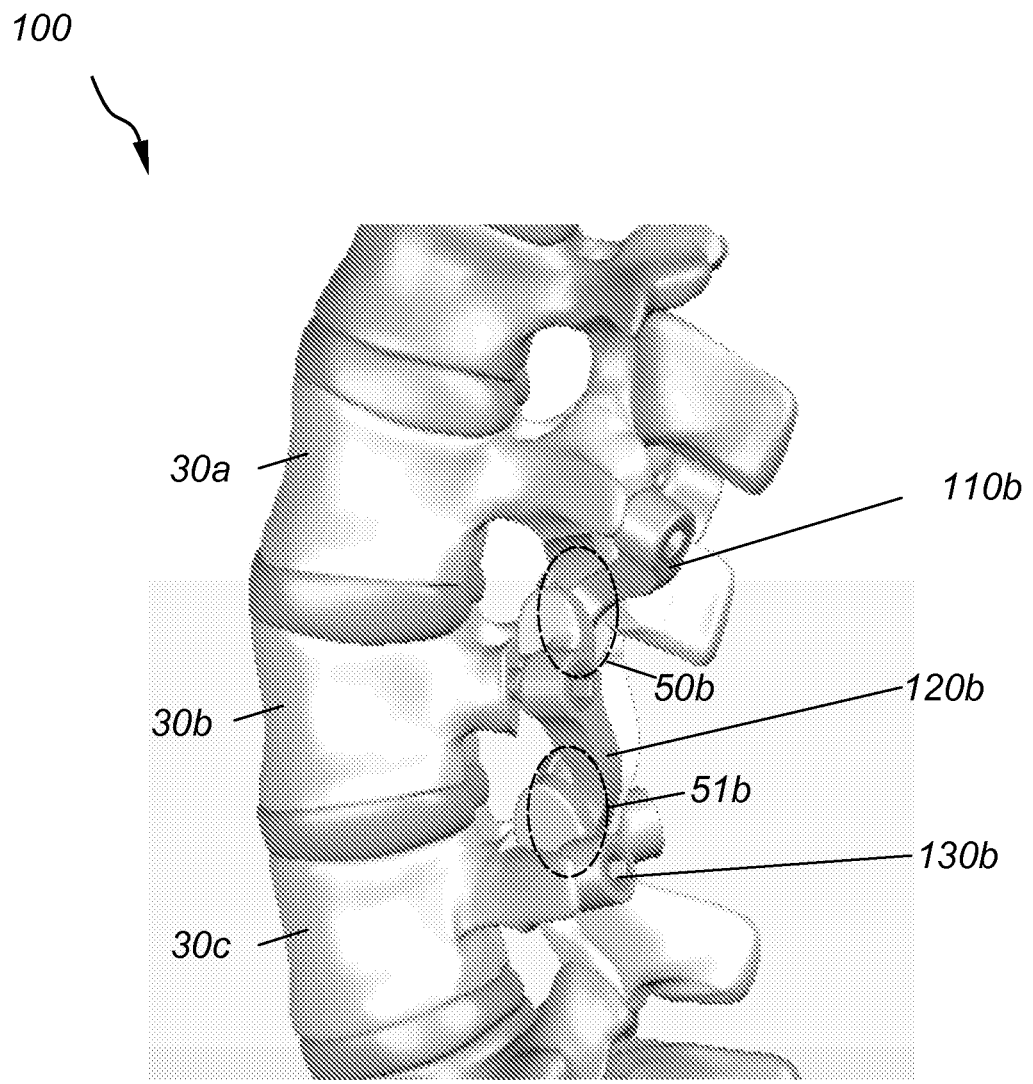
FIG. 6 is a side view of the dynamic facet replacement system of FIG. 5
Figure 7:
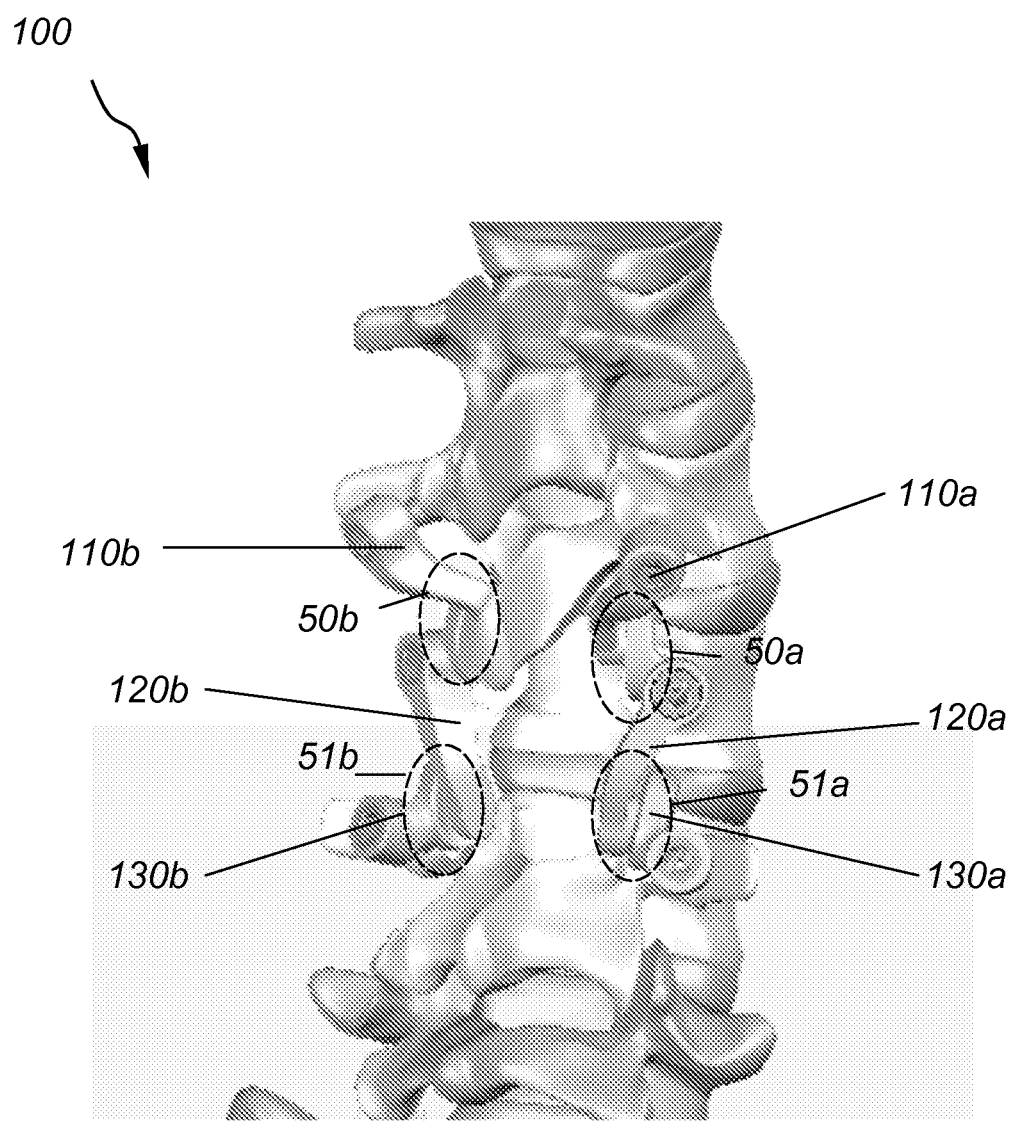
FIG. 7 is another front perspective view of the dynamic facet replacement system of FIG. 5.
Figure 30:
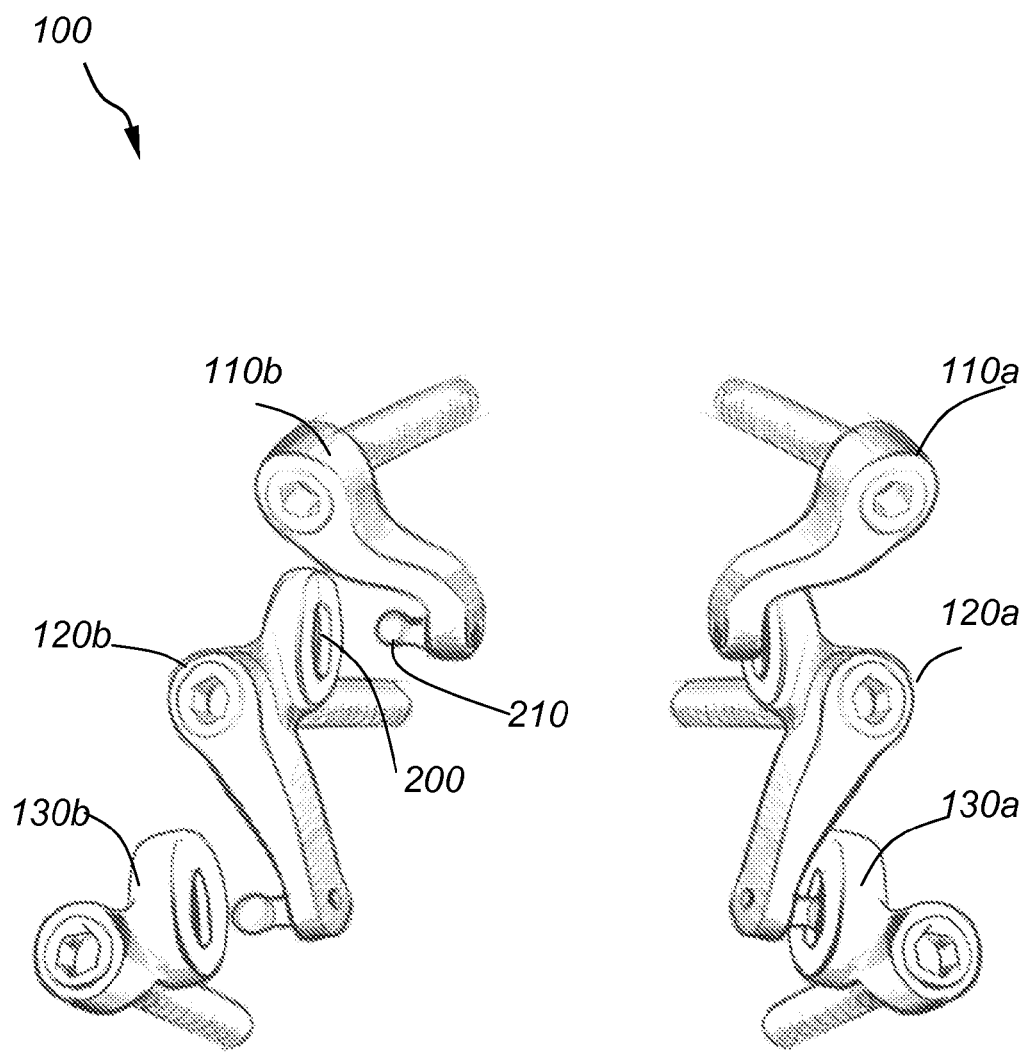
FIG. 30 is detailed view of the facet articulation mechanism.
Figure 31:
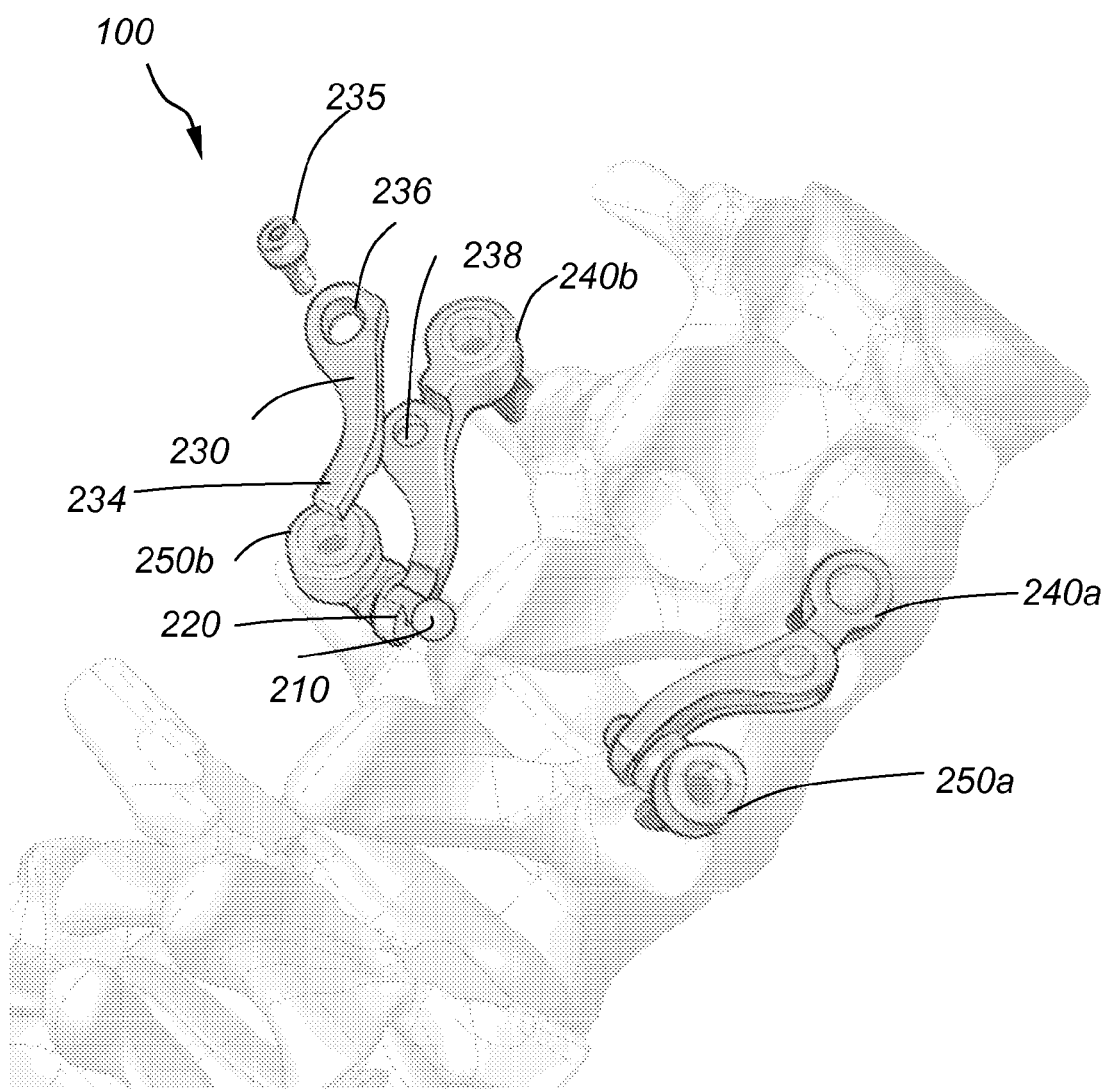
FIG. 31 is another embodiment of a facet articulation mechanism.

Referring to FIG. 5, FIG. 6 and FIG. 7 a dynamic facet replacement system 100 includes an inferior facet replacement assembly 110, pars replacement assembly 120 and a superior facet replacement assembly 130. The inferior facet replacement assembly 110 includes first and second inferior facet replacement components 110a, 110b. The pars replacement assembly 120 includes first and second pars replacement components 120a, 120b. The superior facet replacement assembly includes first and second superior facet replacement components 130, 130b. In the embodiment of FIG. 5 the inferior facet replacement components 110a, 110b articulate with the pars replacement components 120a, 120b, respectively, and the pars replacement components 120a, 120b, articulate with the superior facet replacement components 130a, 130b, respectively, to dynamically stabilize the facet joints 50a, 50b and 51a, 51b between the adjacent vertebras 30a, 30b and 30b, 30c, respectively. In this embodiment the articulation between the inferior facet replacement components or the superior facet replacement components and the pars replacement components is surface to surface articulation. In other embodiments the articulation is a constrained articulation. In one embodiment the constrained articulation is by engaging a male articulation component with a female articulation component, as described in the co-pending patent application Ser. No. 10/660,927 entitled "Apparatus and method for connecting spinal vertebrae", the contents of which are incorporated herein by reference. In the embodiment of FIG. 30 the articulation mechanism is a tongue and groove type articulation. As shown in FIG. 30, one surface includes a groove 240 and the opposite articulating surface includes an extension 210 that fits into the opposite groove to form a tongue and groove type connection. Extension 210 may be snapped in or slidably inserted into the groove 200. In other embodiments, extension 210 is placed in a slot and then rotated to engage and lock into a groove communicating with the slot. Furthermore, in other embodiments any of the described replacement components articulate with the surfaces of the natural facets. In another embodiment of the articulation mechanism, shown in FIG. 31, a first articulating member 250b includes and extension member 210 that fits into a slot 220 of an opposite second articulating member 240b. An elongated locking member 230 fits over the open end of the slot 220 and locks the extension member 210 in the slot 220. The locking member 230 includes an elongated body having a portion 234 that fits over the slot 220 and a portion that includes a through opening 236. Opening 236 is aligned with an opening 238 in the second articulating member 240b and a bolt or screw 235 is inserted into openings 236 and 238 to lock locking member 230 onto articulating member 240*b* and extension member 210 in the slot 220.

Figure 8:
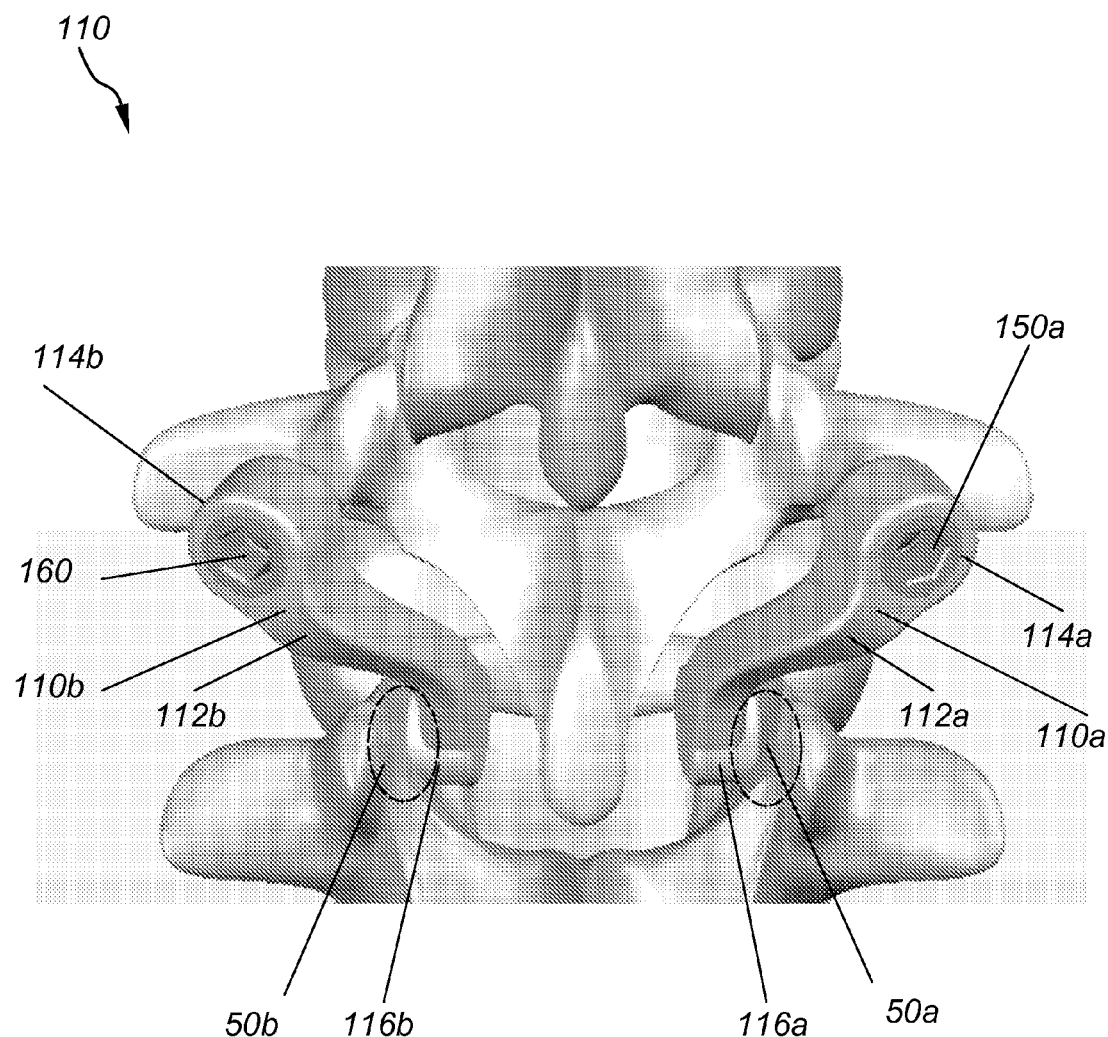
FIG. 8 is a front (posterior) perspective view of the inferior facet replacement assembly.
Figure 9:
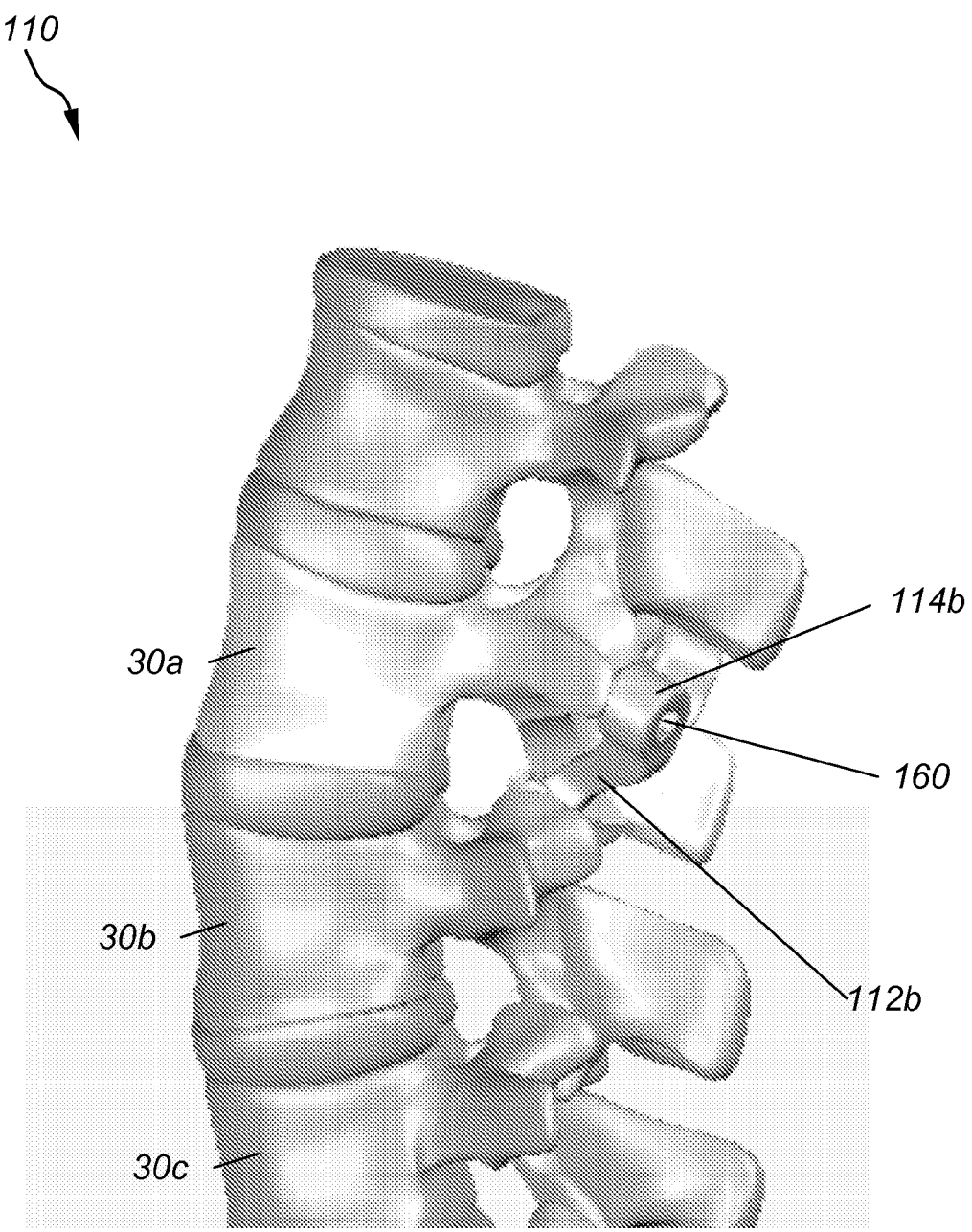
FIG. 9 is a side view of the inferior facet replacement assembly of FIG. 8.
Figure 10A:
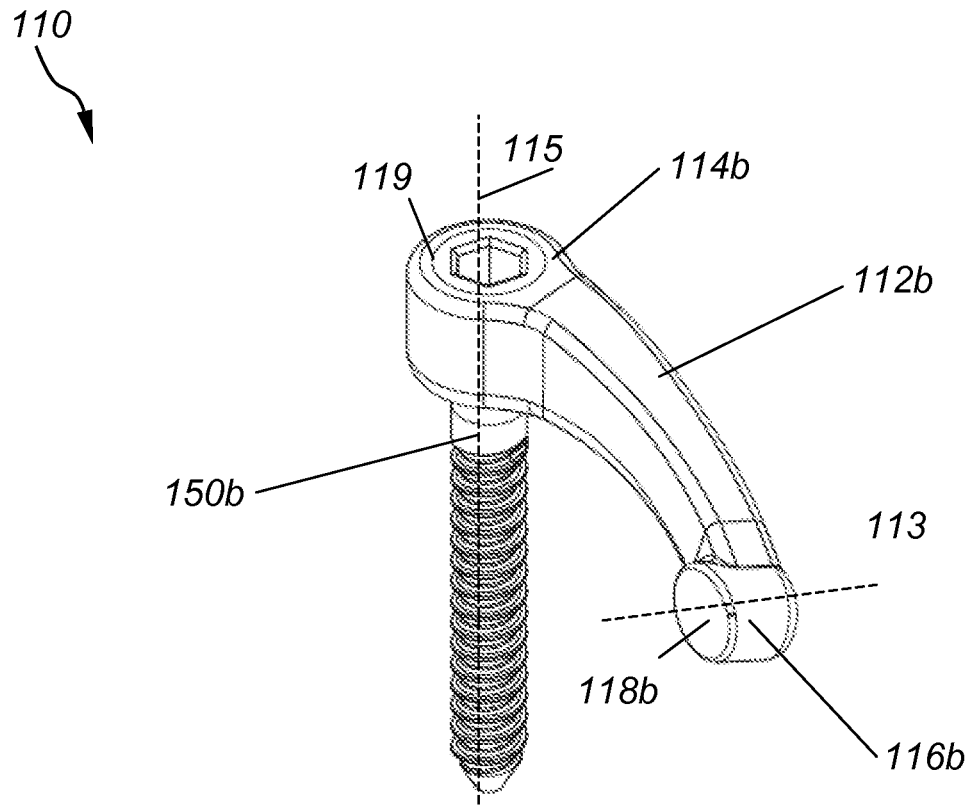
FIG. 10A is a front perspective view of a facet replacement component of FIG. 8.
Figure 10B:
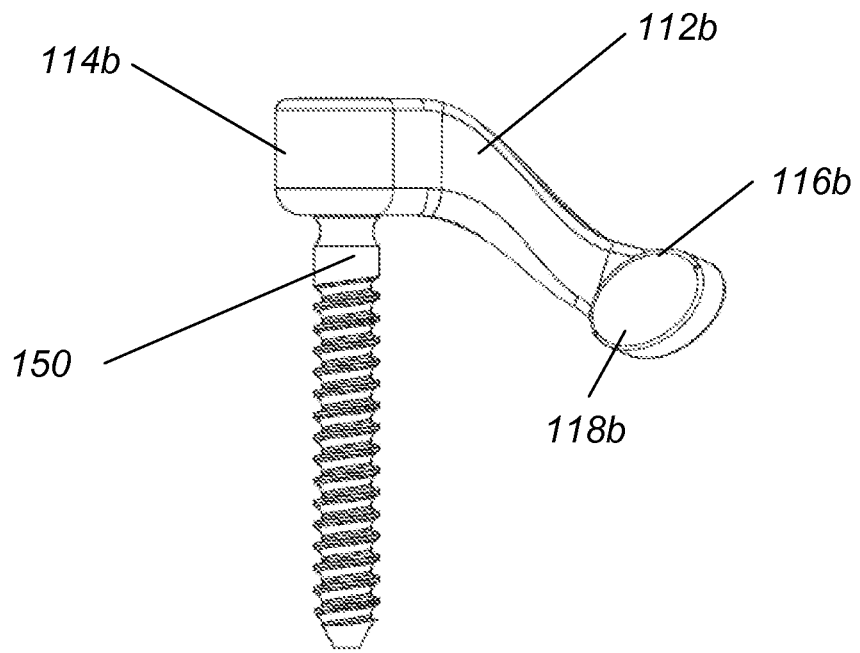
FIG. 10B is a side view of the facet replacement component of FIG. 10A.
Figure 11A:
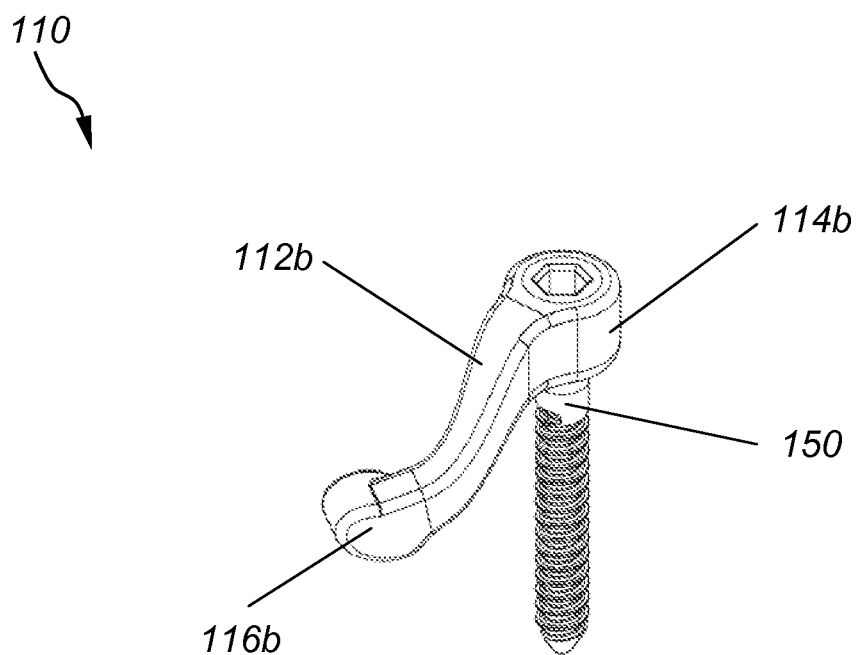
FIG. 11A is another front perspective view of the facet replacement component of FIG. 8.
Figure 11B:
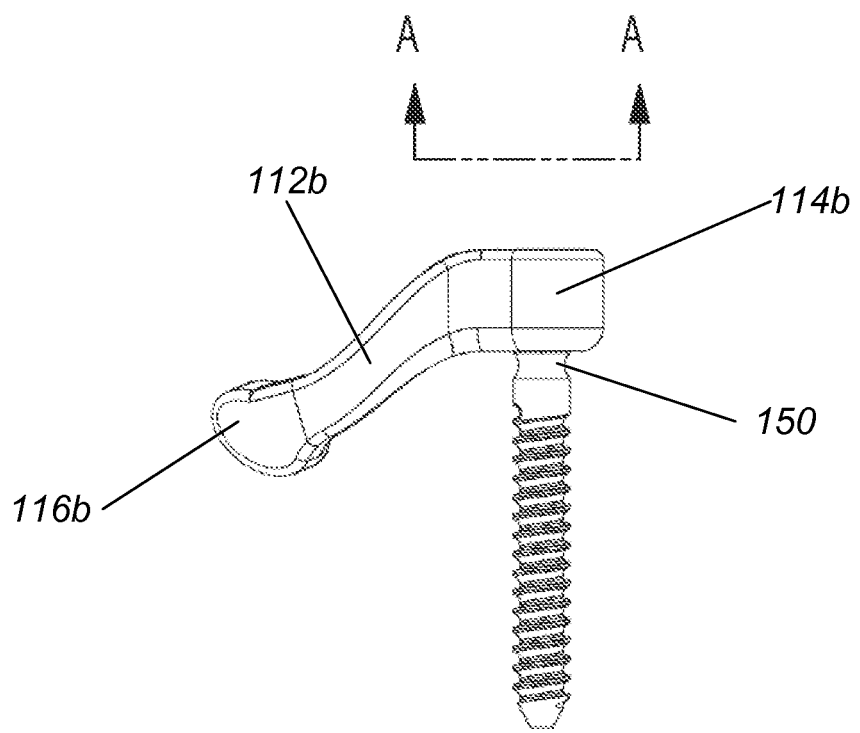
FIG. 11B is a side perspective view of the facet replacement component of FIG. 11A.
Figure 12:
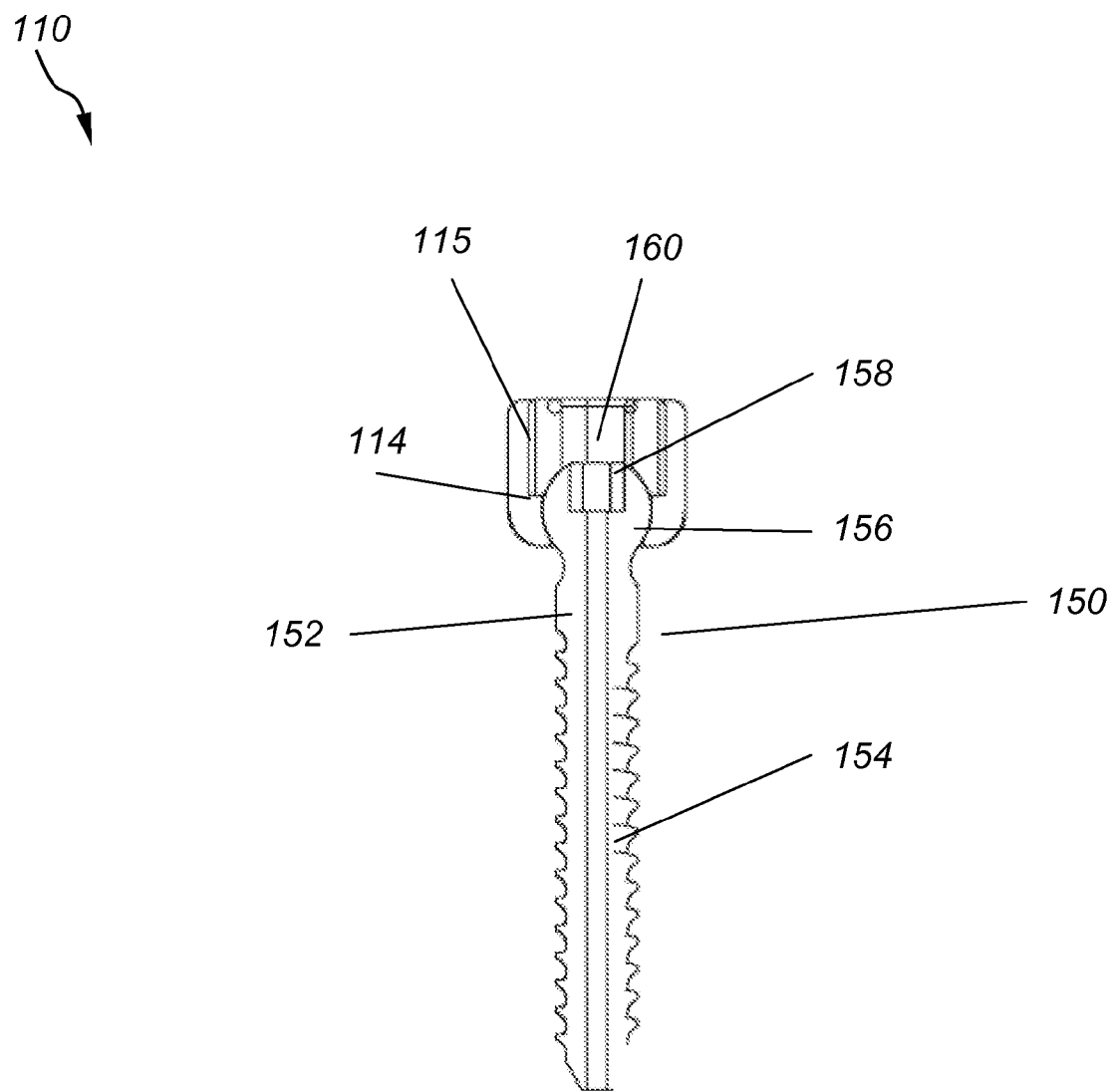
FIG. 12 is a cross-sectional view of the facet replacement component of FIG. 11B along the axis A-A.
Figure 13:
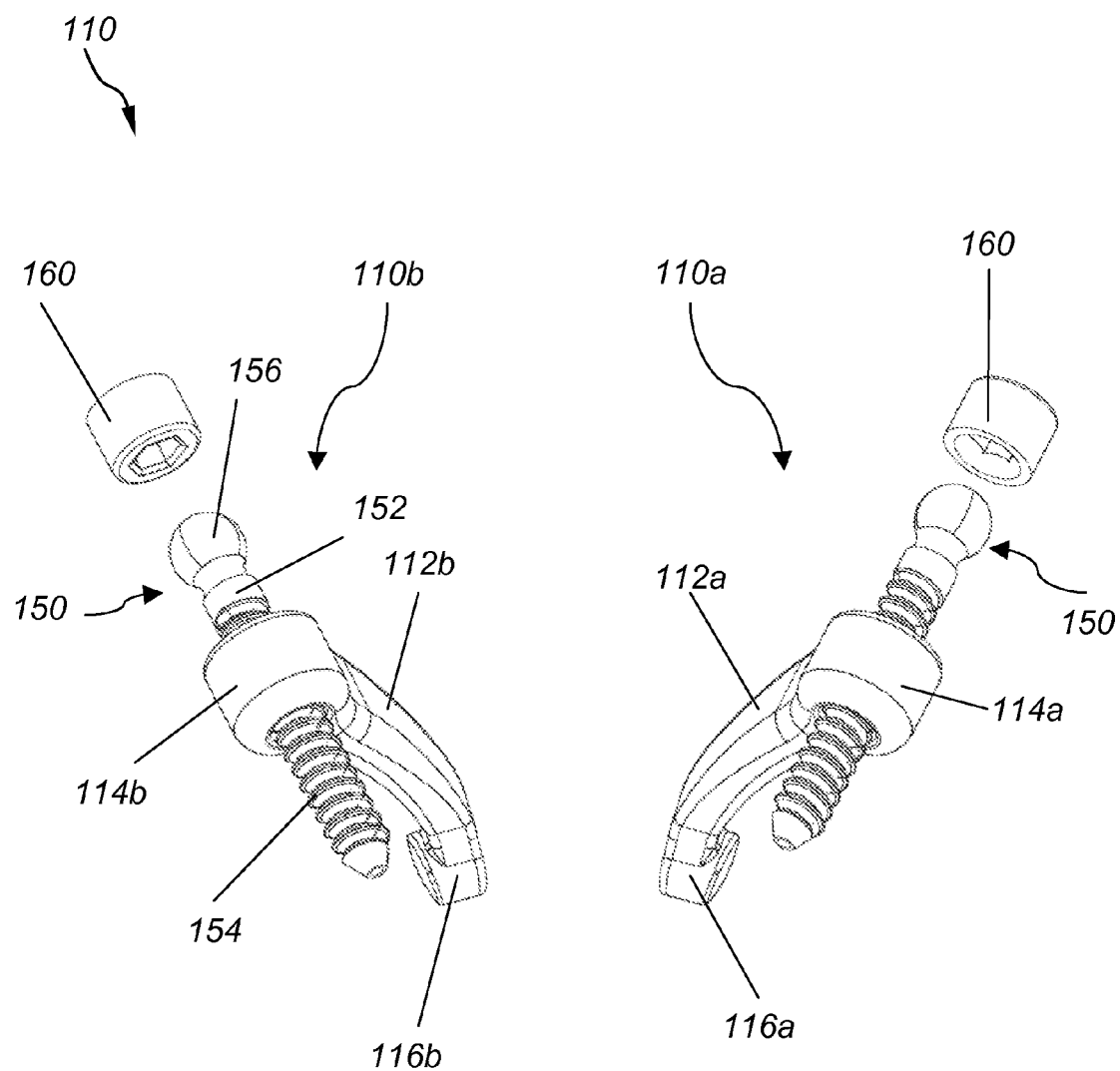
FIG. 13 is a partially exploded anterior view of the inferior facet replacement assembly of FIG. 8.
Figure 14:
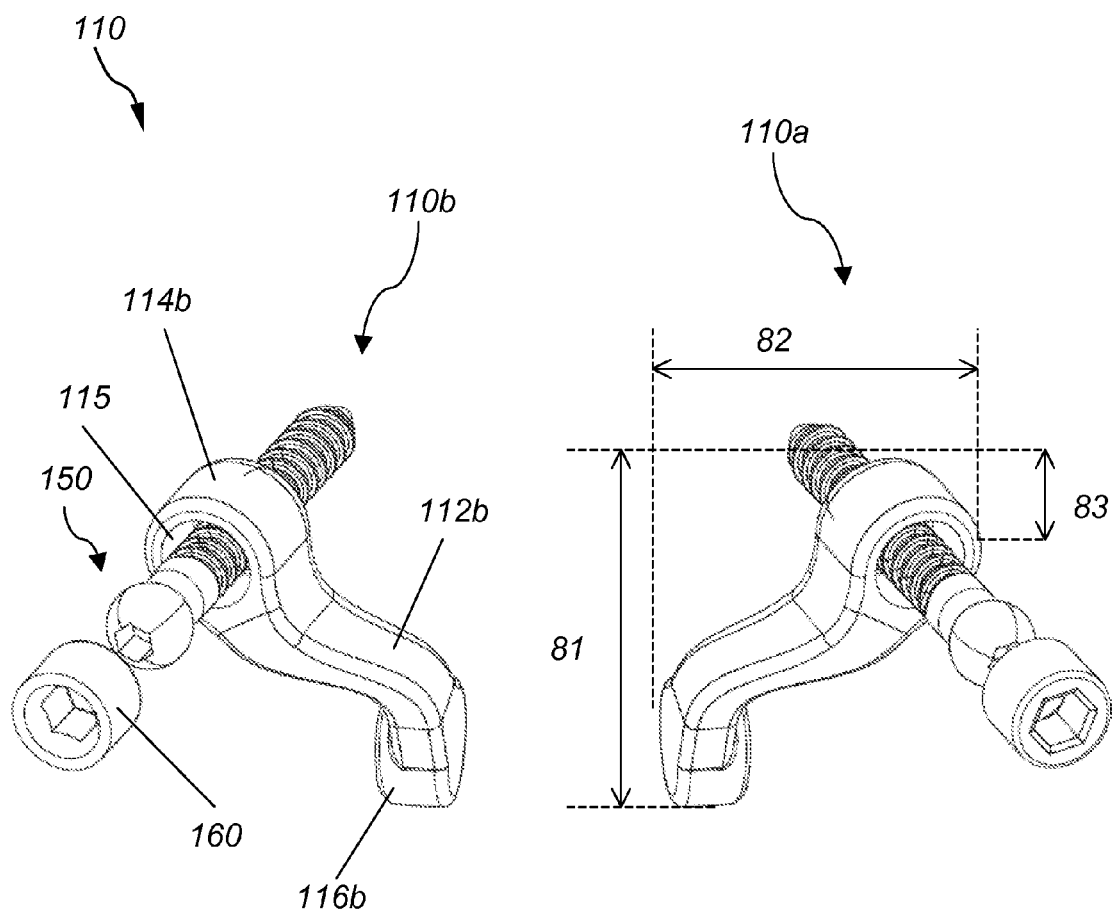
FIG. 14 is a partially exploded posterior view of the inferior facet replacement assembly of FIG. 8.

Referring to FIG. 8 and FIG. 9, the inferior facet replacement assembly 110 includes facet replacement components 110*a*, 110*b* that articulate with facet-like surfaces of the pars 120*a*, 120*b*, respectively, as shown in FIG. 5, or with the natural superior facets 46*a*, 46*b* of the adjacent vertebra 30*b*. Each inferior facet replacement component 110*a*, 110*b*, includes an elongated curved body 112*a*, 112*b* having a cylindrical shaped first end 114*a*, 114*b* and cylindrical shaped second end 116*a*, 116*b*. The axis 113 of the cylindrical shaped second end 116*b* is oriented perpendicular to the axis 115 of the cylindrical shaped first end 114*a*, as shown in FIG. 10A. The cylindrical second end 116*b* extends away from the main body 112*b* and has a portion that overhangs in the direction of 113*b*. The cylindrical second end 116*b* has an elliptical first surface 118*b* configured to articulate with the natural superior facet or any other facet-like surface. The cylindrical shaped first end 114*b* has a through opening 119 dimensioned to receive a fixation element 150*b*. In the example of FIG. 8 the fixation element 150 is an elongated poly-axial screw and is used to anchor the facet replacement component 110*b* to pedicle 48*b* of the vertebra 30*a*. The poly-axial screw 150 includes a spherical head 156 and an elongated body 152 having outer threads 154. The spherical head 156 includes a cutout 158 on the top dimensioned and configured to receive a screwdriver, shown in FIG. 12. Once the screw is anchored in the desired vertebral location, the cylindrical shaped first end 114*b* is rotated and oriented to position the main body 112*b* so that the elliptical surface 118*b* of the second cylindrical end 116 articulates with a facet-like surface of the replacement par or a natural facet. Once the desired orientation of the main body 112*b* is set, the first cylindrical shaped end 114*b* is secured onto the spherical screw head 156 with a set screw 160, as shown in FIG. 12 and FIG. 13. Other vertebral locations where the fixation element 150 may be anchored include the vertebral body, lamina or the processes.

Figure 15:
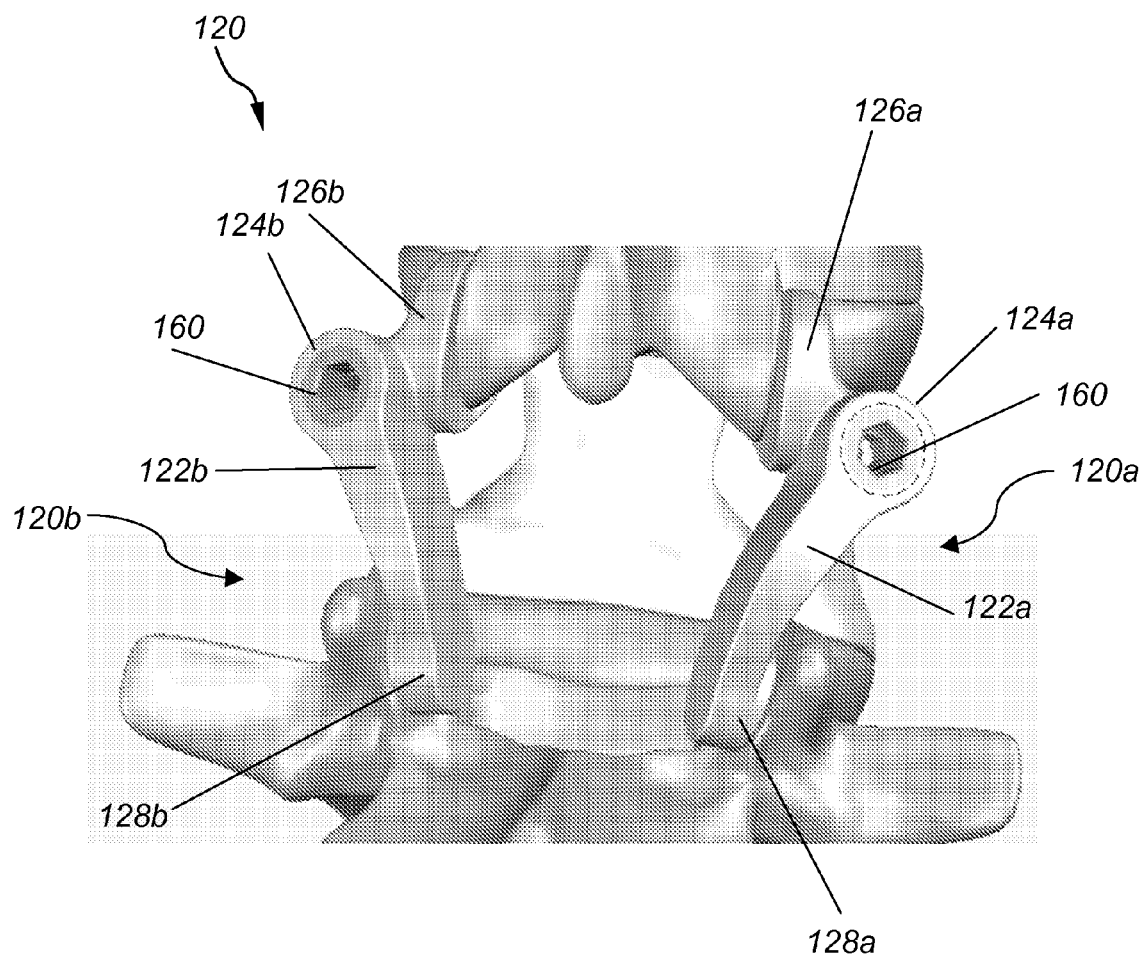
FIG. 15 is a front (posterior) perspective view of the pars replacement assembly.
Figure 16:
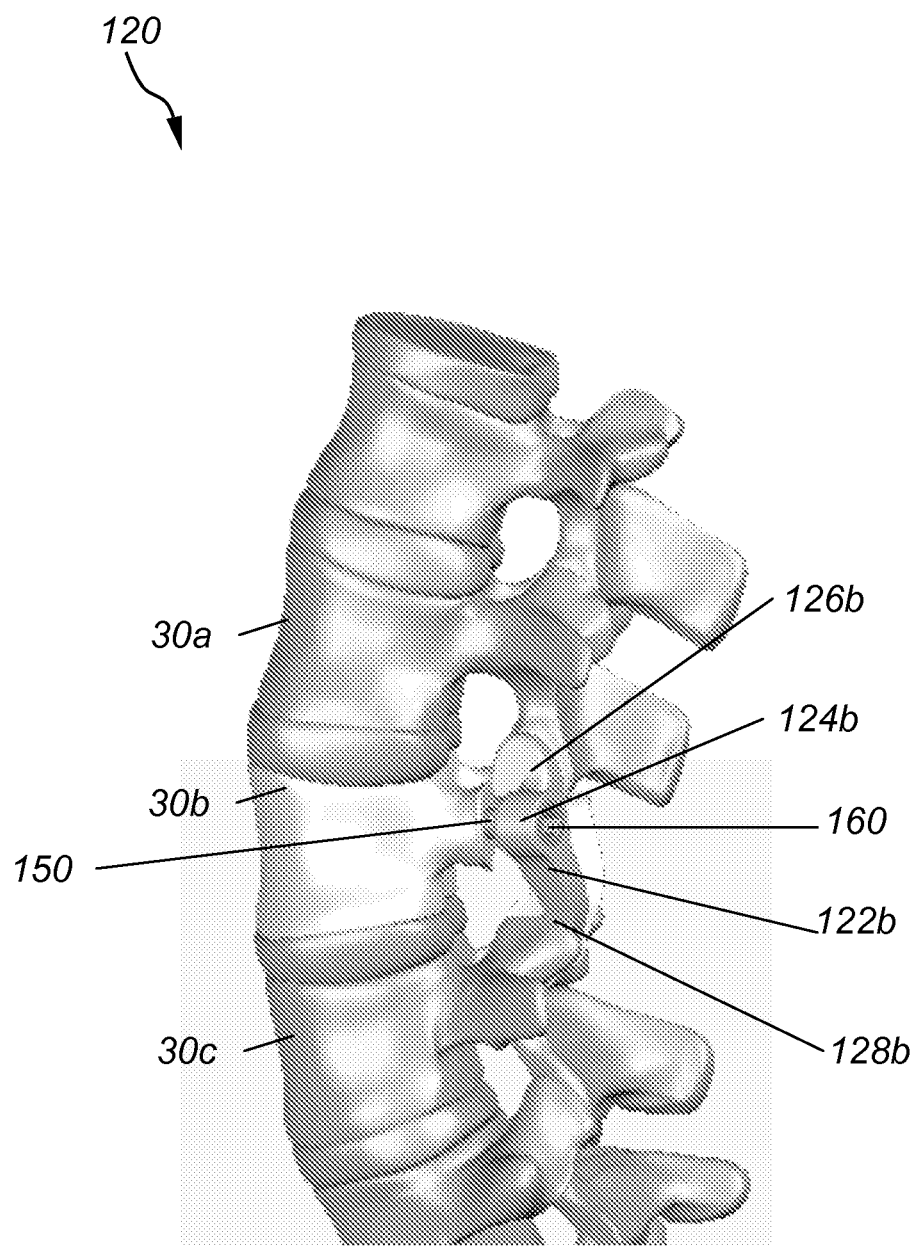
FIG. 16 is a side perspective view of the pars replacement assembly of FIG. 15.
Figure 17:
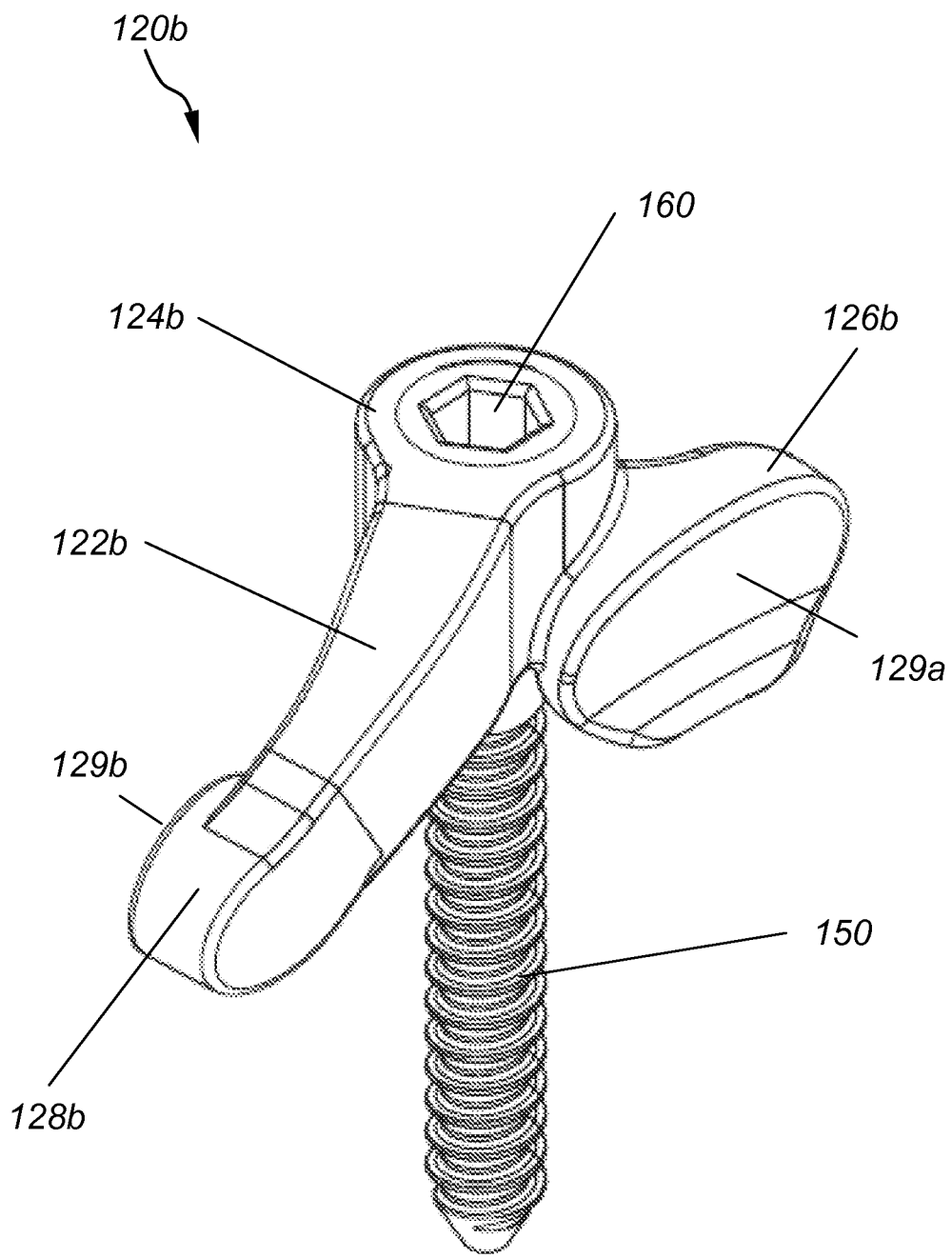
FIG. 17 is front perspective view of a pars replacement component of FIG. 15.
Figure 18:
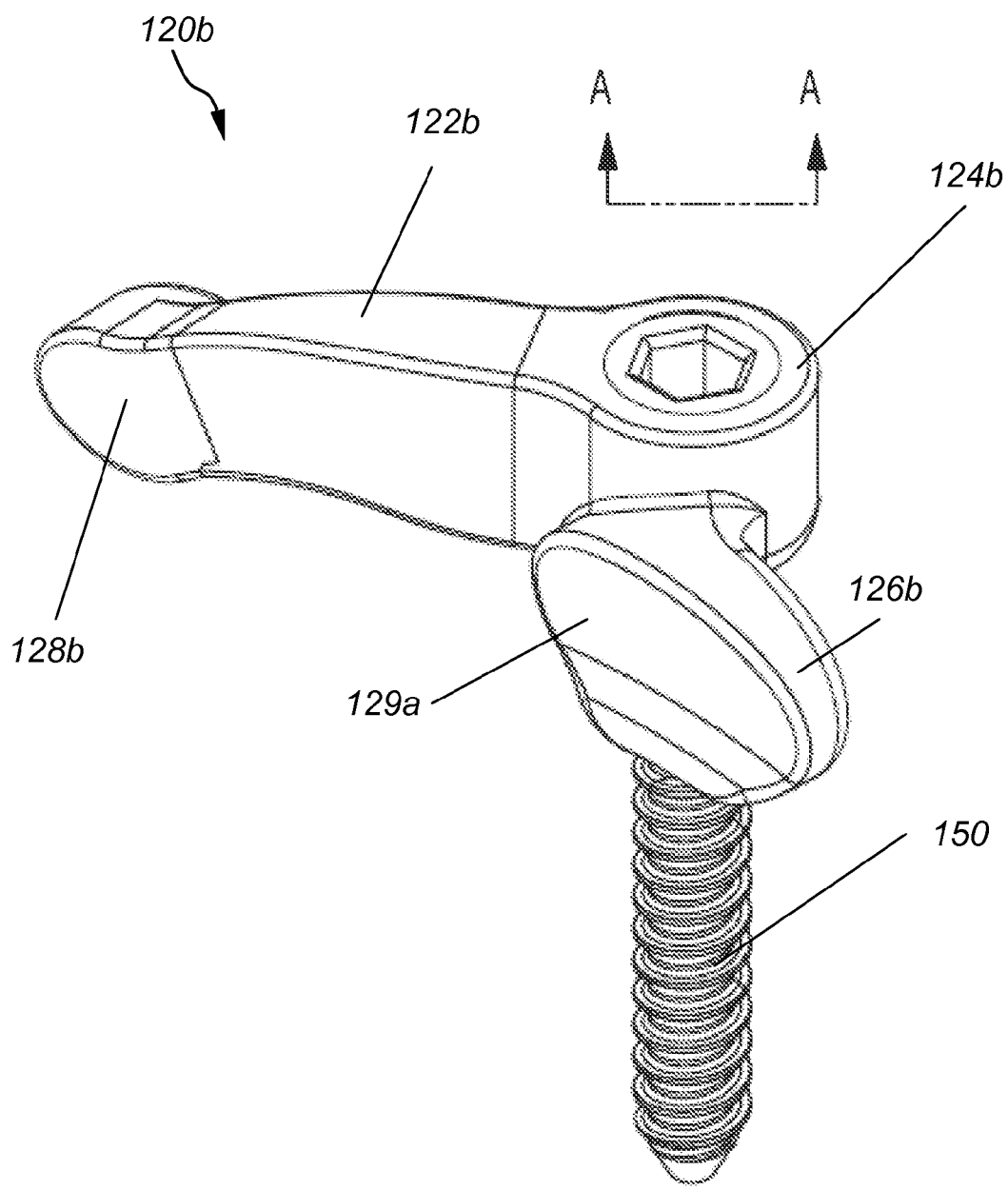
FIG. 18 is side perspective view of the pars replacement component of FIG. 17.
Figure 19:
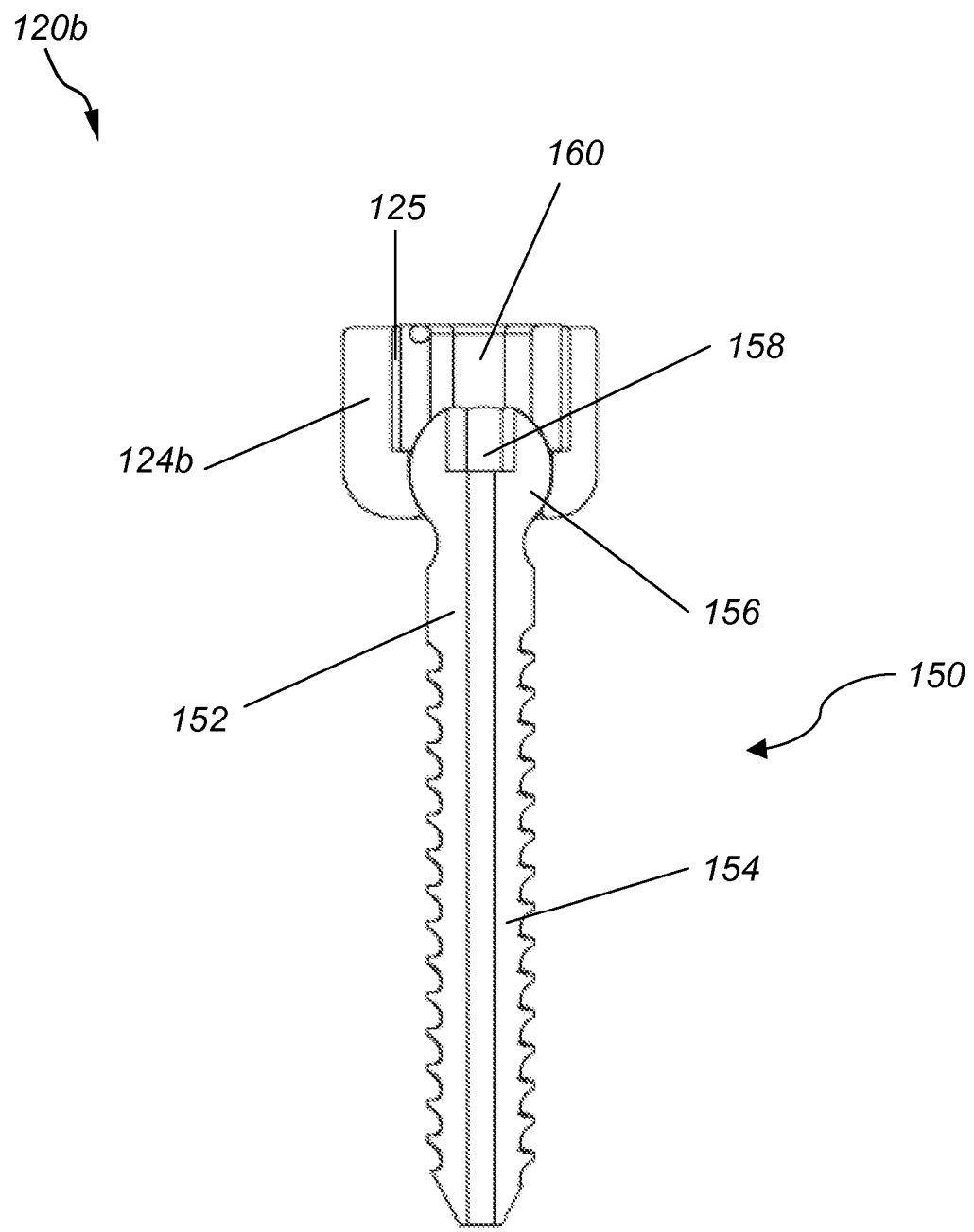
FIG. 19 is a cross-sectional view of the pars replacement component of FIG. 18 along the A-A axis.
Figure 20:
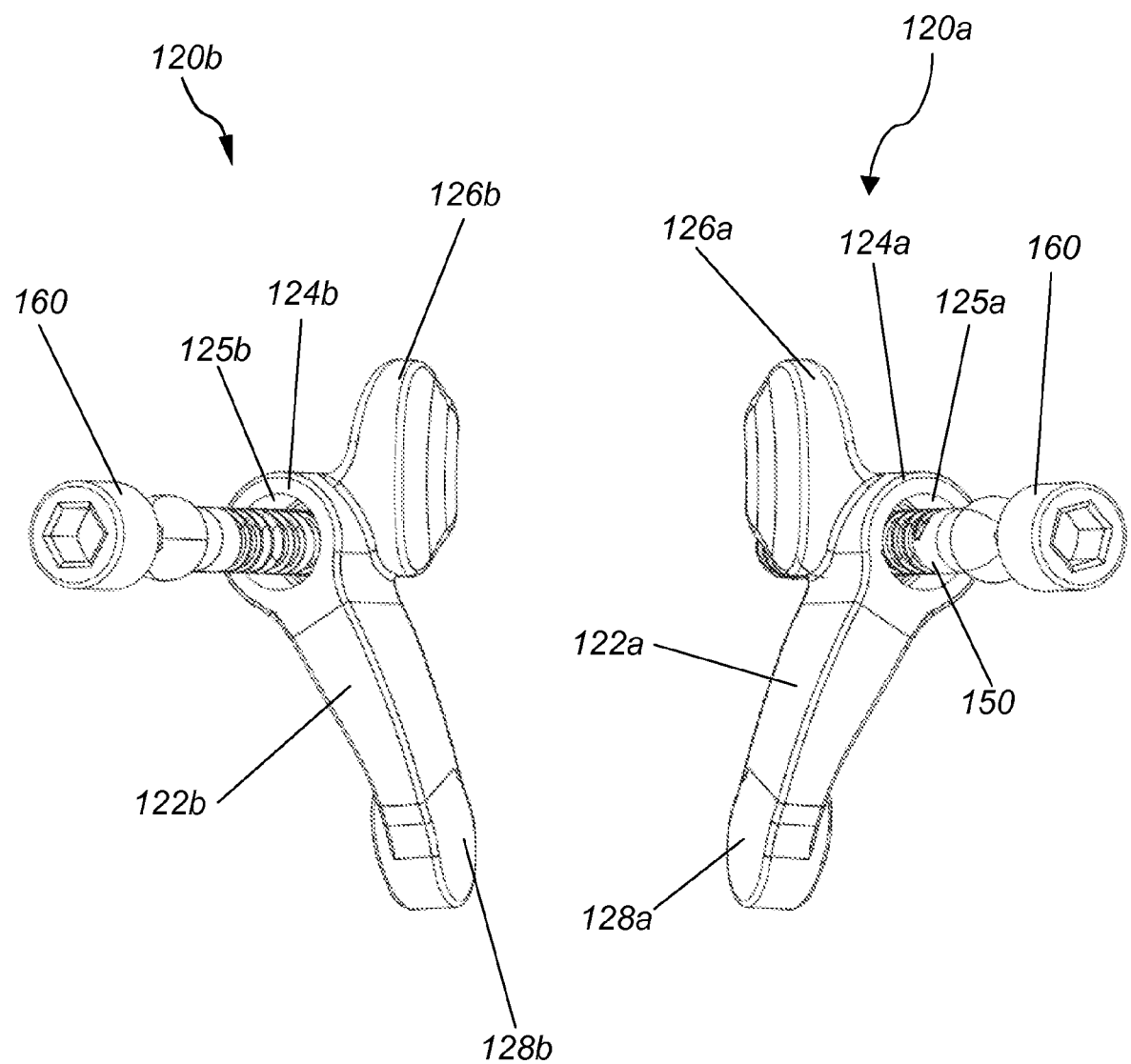
FIG. 20 is a partially exploded posterior view of the pars replacement assembly of FIG. 15.

Referring to FIG. 15 and FIG. 16, the pars replacement assembly 120 includes pars replacement components 120*a*, 120*b* that articulate with facet-like surfaces of the superior and inferior facet replacement components 110*a*, 110*b*, and 130*a*, 130*b*, respectively, as shown in FIG. 5, or with the natural superior facets 46*a*, 46*b* and inferior facets 45*a*, 45*b* of the adjacent vertebras 30*a*, 30*c*, respectively. Each par replacement component 120*a*, 120*b*, includes an elongated curved body 122*a*, 122*b* having a cylindrical shaped first end 124*a*, 124*b* and cylindrical shaped second end 128*a*, 128*b*. The axis 123 of the cylindrical shaped second end 128*b* is oriented perpendicular to the axis 125 of the cylindrical shaped first end 124*b*, as shown in FIG. 17. The cylindrical first end 124*b* also includes a wing-like extension 126*b* having an elliptical surface 129*a* configured to articulate with a facet-like surface of an inferior facet replacement component or a natural inferior facet. The cylindrical second end 128*b* extends away from the main body 122*b* and has a portion that overhangs in the direction of 123*b*. The cylindrical second end 128*b* has an elliptical first surface 129*b* configured to articulate with a facet-like surface of the superior facet replacement component, shown in FIG. 5 or a natural superior facet. The cylindrical shaped first end 124*b* has a through opening 89 dimensioned to receive a fixation element 150. In the example of FIG. 17 the fixation element 150 is an elongated poly-axial screw and is used to anchor the par replacement component 110*b* to pedicle 48*b* of the vertebra 30*b*. The poly-axial screw 150 includes a spherical head 156 and an elongated body 152 having outer threads 154. The spherical head 156 includes a cutout on the top 158 dimensioned and configured to receive a screwdriver. Once the screw is anchored in the desired vertebral location, the cylindrical shaped first end 124*b* is rotated and oriented to position the main body 122*b* so that the elliptical surfaces 129*a* of the wing-like extension of the first end and 129*b* of the second cylindrical end 128*b* articulate with facet-like surfaces of the inferior facet replacement component and the superior facet replacement component, respectively, or the inferior and superior natural facets. Once the desired orientation of the main body 122*b* is set, the first cylindrical end is secured onto the spherical screw head 150 with a setscrew 160, as shown in FIG. 20.

Figure 21:
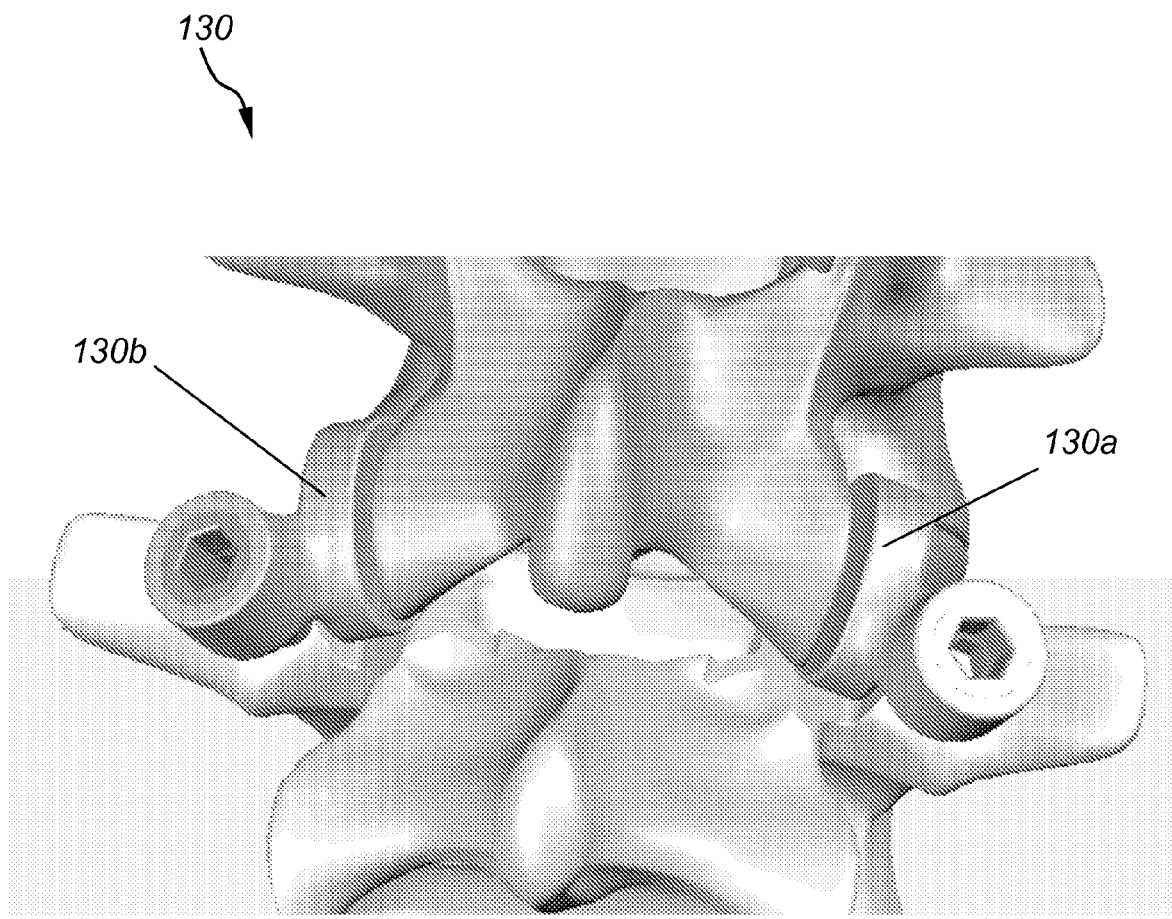
FIG. 21 is a front (posterior) perspective view of the superior facet replacement assembly.
Figure 22:
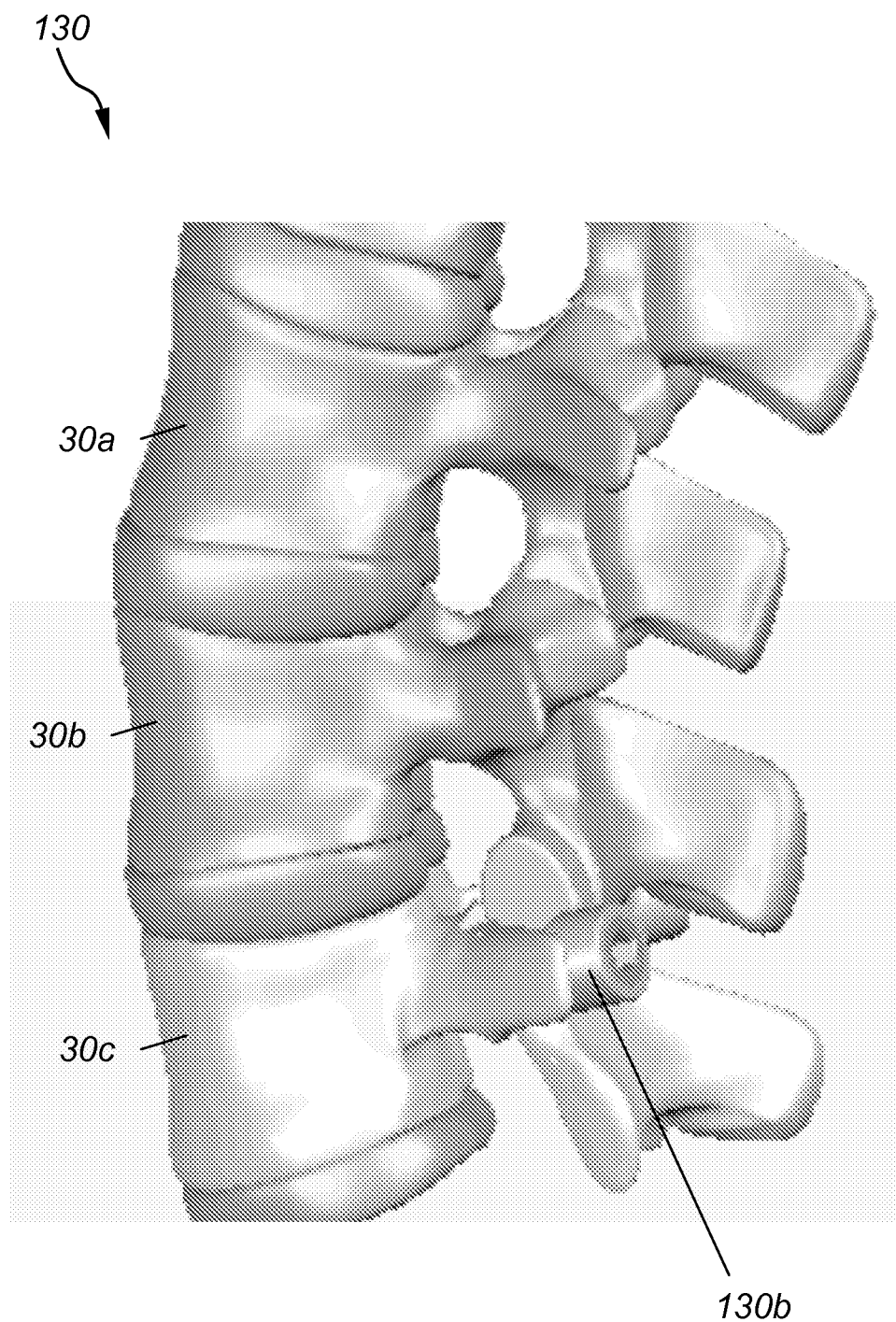
FIG. 22 is a side perspective view of the superior facet replacement assembly of FIG. 21.
Figure 23:
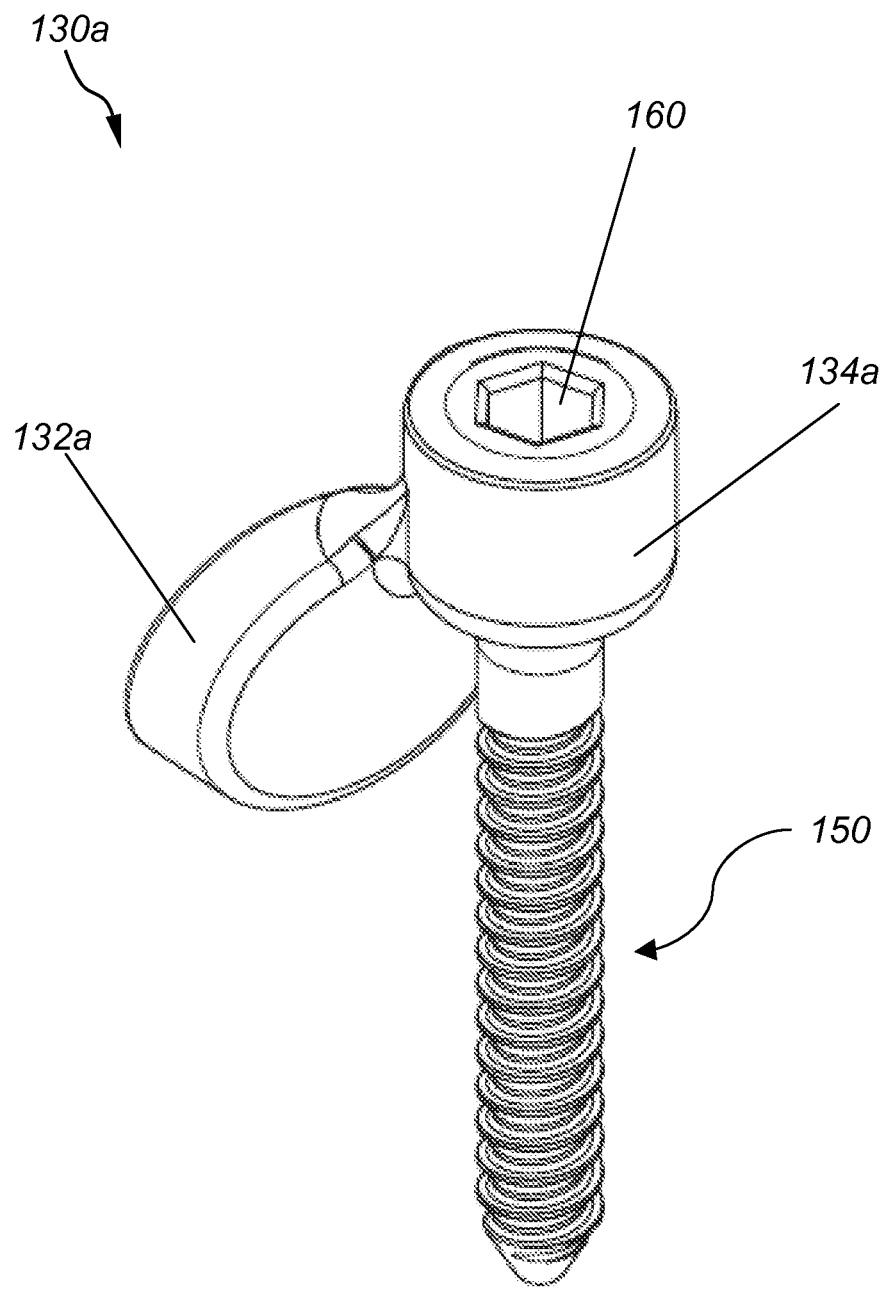
FIG. 23 is a front perspective view of a superior facet replacement component of FIG. 21.
Figure 24:
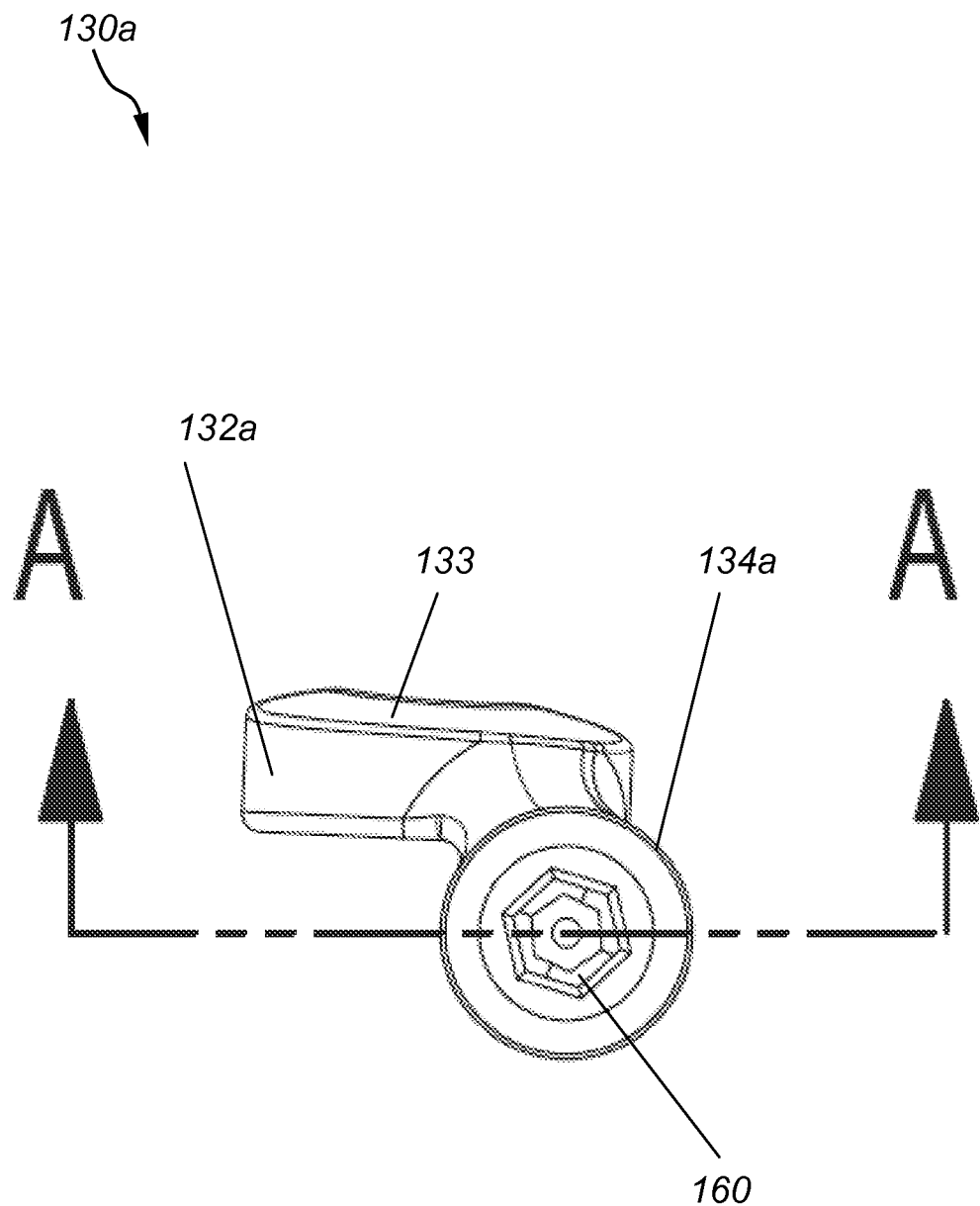
FIG. 24 is a top view of the superior facet replacement component of FIG. 23.
Figure 25:
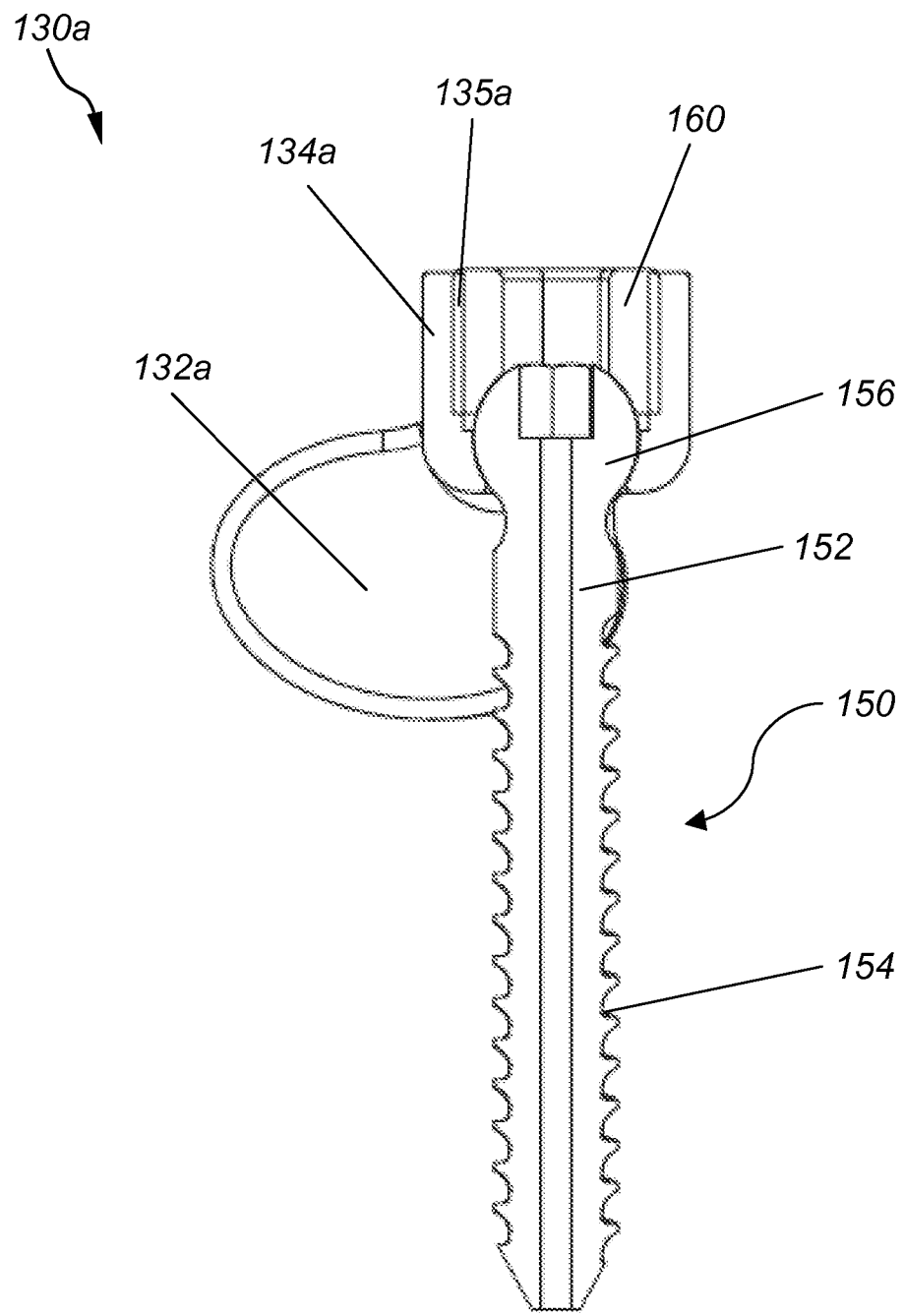
FIG. 25 is a cross-sectional view of the superior facet replacement component of FIG. 24 along the A-A axis.
Figure 26:
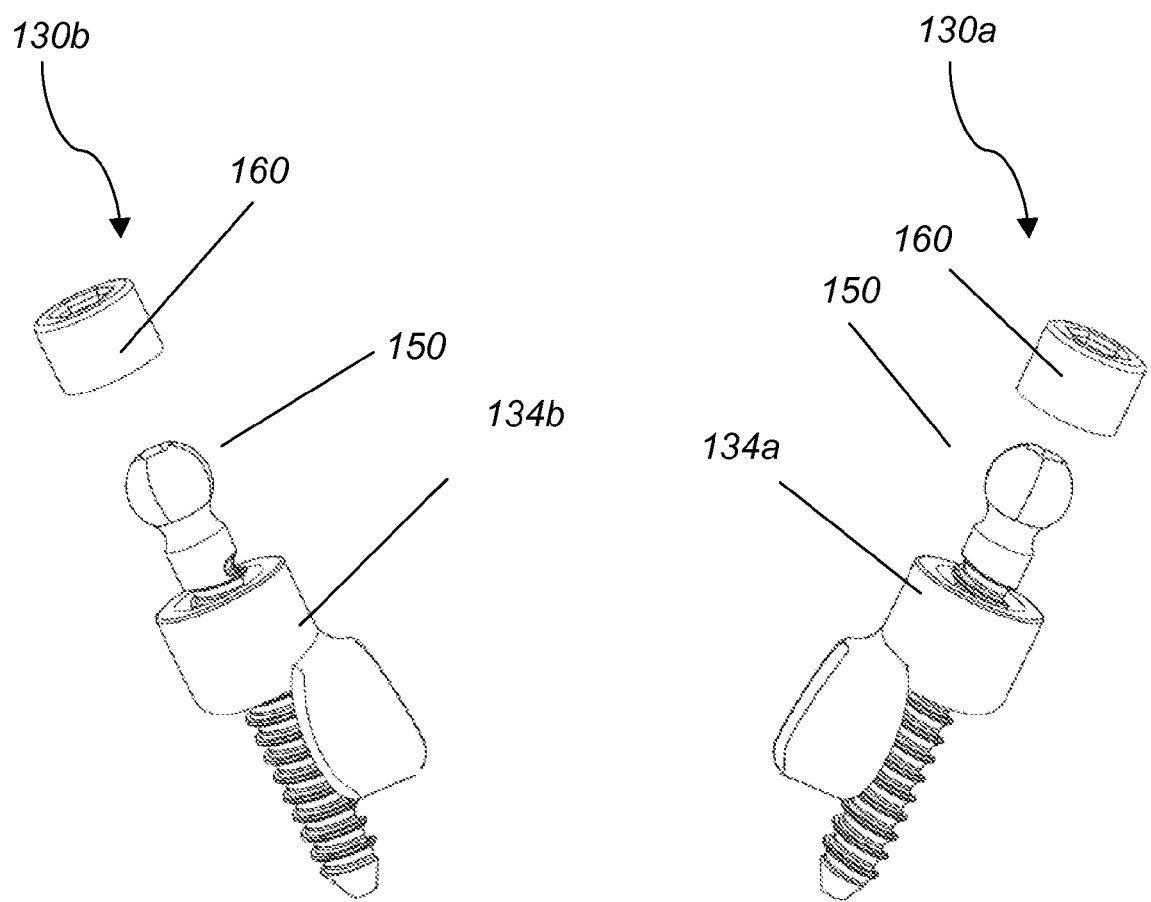
FIG. 26 is a partially exploded view of the superior facet replacement assembly of FIG. 21.
Figure 27:
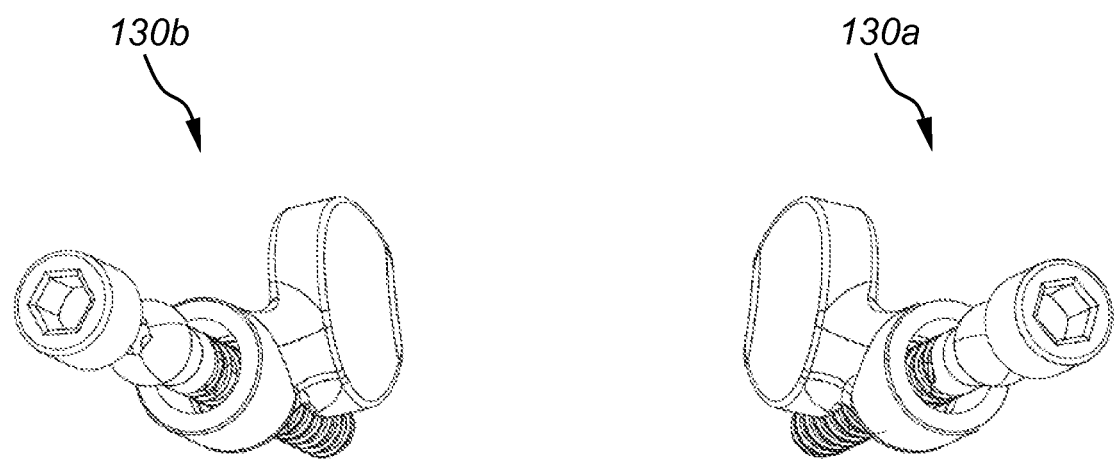
FIG. 27 is a top view of the partially exploded superior facet replacement assembly of FIG. 26.
Figure 28:
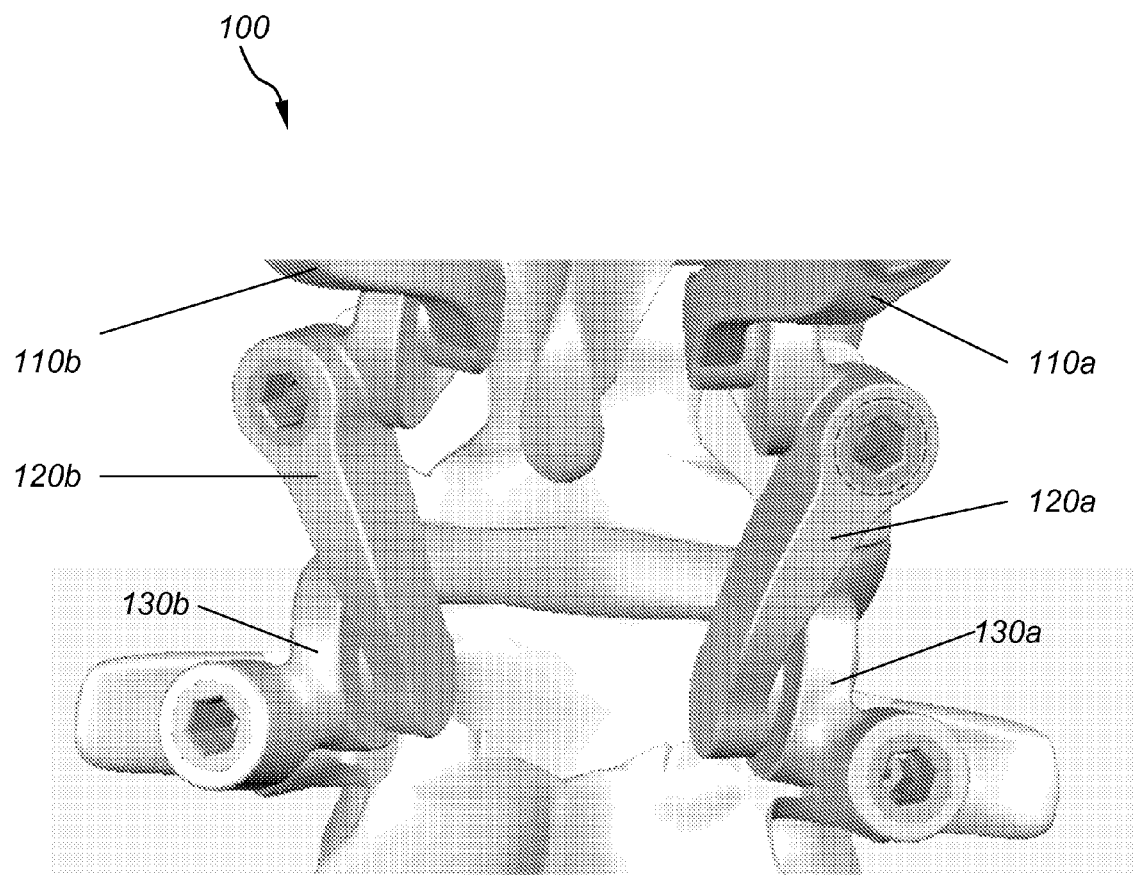
FIG. 28 is a front (posterior) perspective view of the interfaces (joints) between the pars assembly with the superior facet replacement assembly and the pars assembly with the inferior facet replacement assembly.

Referring to FIG. 21 and FIG. 22, the superior facet replacement assembly 130 includes superior facet replacement components 130*a*, 130*b* that articulate with facet-like surfaces of the pars 120*a*, 120*b*, respectively, as shown in FIG. 5 and FIG. 28, or with the natural inferior facets 45*a*, 45*b* of the adjacent vertebra 30*b*. Each superior facet replacement component 130*a*, 130*b*, includes a cylindrical shaped first end 134*a*, 134*b* and a wing-like extension 132*a*, 132*b*, extending from the cylindrical shaped first end 134*a*, 134*b*, respectively. The wing-like extension 132*a* has an elliptical surface 133*a* configured to articulate with a facet-like surface of an inferior facet replacement component, or par replacement component or a natural inferior facet. The cylindrical shaped first end 134*a* has a through opening 139 dimensioned to receive a fixation element 150. In the example of FIG. 23 the fixation element 150 is an elongated poly-axial screw and is used to anchor the facet replacement component 130*a* to pedicle 48*a* of the vertebra 30*c*. The poly-axial screw 150 includes a spherical head 156 and an elongated body 152 having outer threads 154. The spherical head 156 includes a cutout on the top 158 dimensioned and configured to receive a screwdriver. Once the screw is anchored in the desired vertebral location, the cylindrical shaped first end 134*a* is rotated and oriented so that the elliptical surface 133*a* of the wing-like structure 132*a* articulates with a facet-like surface of the replacement par or a natural facet. Once the desired orientation of the elliptical surface 133*a* is set, the first cylindrical end is secured onto the spherical screw head 156 with a setscrew 160, as shown in FIG. 26.

Figure 29:
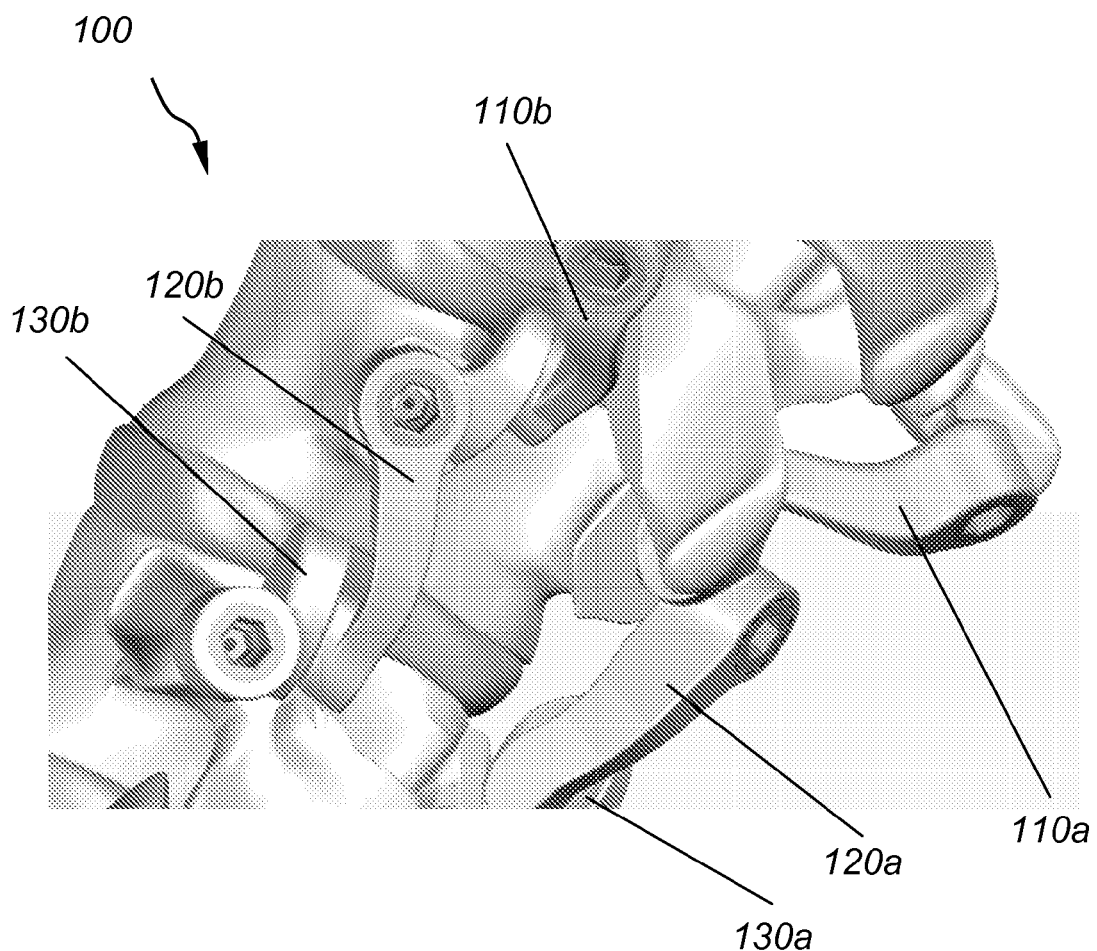
FIG. 29 is a side perspective view of FIG. 28.

The superior replacement components 130*a*, 130*b* articulate with the par replacement components 120*a*, 120*b*, respectively, to form facet joint 51*a*, 51*b* and the par replacement components 120*a*, 120*b* articulate with the inferior replacement components 110*a*, 11*b*, respectively, to form facet joints 50*a*, 50*b*, as shown in FIG. 5, FIG. 28 and FIG. 29.

Other embodiments are within the scope of the following claims. The facet replacement components and the par replacement components are made of metal, plastic, ceramic, bone, polymers, composites, absorbable material, biodegradable material, or combinations thereof. The articulating surfaces may be flat or slightly curved. The articulation may be a constrained articulation, as was described above. The facet replacement components may have adjustable lengths. The facet replacement system may be extended in either caudad 272 or cephalad 270 directions Several embodiments of the present invention have been described. Nevertheless, it will be understood that various modifications may be made without departing from the spirit and scope of the invention. Accordingly, other embodiments are within the scope of the following claims.

What is claimed is:

1. A dynamic facet replacement system configured to articulately connect a first spinal vertebra to an adjacent second spinal vertebra and said second spinal vertebra to an adjacent third spinal vertebra, along the natural facet joints comprising:
- first and second inferior facet components configured to replace left and right natural inferior facets of a first vertebra, respectively;
- first and second par components configured to replace left and right natural pars of a second vertebra, respectively;
- first and second superior facet components configured to replace left and right natural facets of a third vertebra, respectively;
- wherein each of said inferior and superior facet components comprises a facet articulating surface and each of said par components comprises first and second par articulating surfaces, wherein said first and second par articulating surfaces are opposite to each other;
- wherein said first and second par components are shaped and dimensioned to be inserted between said first and second inferior and superior facet components, respectively, and to articulately connect said first and second inferior facet components to said first and second superior facet components, respectively, by connecting said first and second par articulating surfaces to said facet articulating surfaces of the inferior and superior facet components, respectively;
- wherein each of said inferior facet components comprises an elongated curved body extending along a first axis and said body comprises a first cylindrical shaped end, configured to be attached to a location of said first vertebra and a second cylindrical shaped end comprising said inferior facet articulating surface and extending from said elongated curved body perpendicular to said axis; and
- wherein in each of said inferior facet components, said first cylindrically shaped end's axis is oriented perpendicular to said second cylindrical shaped end's axis and perpendicular to said elongated curved body's first axis.

2. The dynamic facet replacement system of claim 1 wherein said connection of said par components to said inferior and superior facet components comprises a surface-to-surface articulation mechanism.

3. The dynamic facet replacement system of claim 1 wherein said connection of said par components to said inferior and superior facet components comprises a constrained articulation mechanism.

4. The dynamic facet replacement system of claim 3 wherein said constrained articulation mechanism comprises a male articulation component engaging a female articulation component.

5. The dynamic facet replacement system of claim 4 wherein each of said inferior facet components comprises a first extension member protruding from said inferior facet articulating surface and each of said par components comprises a first groove formed in said first par articulating surface and wherein said first groove is shaped and dimensioned to receive said first extension member and thereby to articulately connect said inferior facet component to said par component.

6. The dynamic facet replacement system of claim 5 wherein each of said par components further comprises a second extension member protruding from said second par articulating surface and wherein said superior facet component comprises a second groove formed in said superior facet articulating surface and wherein said second groove is shaped and dimensioned to receive said second extension member and thereby to articulately connect said superior facet component to said par component.

7. The dynamic facet replacement system of claim 6 wherein each of said par components comprises an elongated curved body extending along a second axis and said body comprises a first cylindrical shaped end, configured to be attached to a location of said second vertebra, a second cylindrical shaped end comprising said second par articulating surface, and wherein said first cylindrically shaped end further comprises a wing extension comprising said first par articulating surface.

8. The dynamic facet replacement system of claim 7 wherein in each of said par components said first cylindrically shaped end's axis is oriented perpendicular to said second cylindrical shaped end's axis and perpendicular to said elongated curved body's second axis.

9. The dynamic facet replacement system of claim 8 wherein each of said superior facet components comprises a cylindrically shaped end, configured to be attached to a location of said third vertebra and wherein said cylindrically shaped end further comprises a wing extension comprising said superior facet articulating surface.

10. The dynamic facet replacement system of claim 9 wherein any of said cylindrically shaped ends is configured to be attached to said vertebral locations via a poly-axial screw.

11. The dynamic facet replacement system of claim 10 wherein any of said vertebral locations comprise one of a pedicle, transverse processes, facets, pars interarticularis, intervertebral disc, lamina, or vertebral body.

12. The dynamic facet replacement system of claim 4 wherein said male articulation component comprises an extension member and said female articulation member comprises a slot shaped and dimensioned to receive said extension member.

13. The dynamic facet replacement system of claim 1 comprising at least one of metal, plastic, ceramic, bone, polymers, composites, absorbable material, biodegradable material, or combinations thereof.

14. The dynamic facet replacement system of claim 1 wherein any of said vertebras comprises one of cervical, thoracic, lumbar or sacrum vertebras.

15. A method for articulately connecting a first spinal vertebra to an adjacent second spinal vertebra and said second spinal vertebra to an adjacent third spinal vertebra, along the natural facet joints comprising:
- providing first and second inferior facet components configured to replace left and right natural inferior facets of a first vertebra, respectively, and wherein each of said inferior facet components comprises an articulating surface;
- attaching said first and second inferior facet components to first and second locations of said first vertebra, respectively;
- providing first and second par components configured to replace left and right natural pars of a second vertebra, respectively, and wherein each of said par components comprises first and second par articulating surfaces, and wherein said first and second par articulating surfaces are opposite to each other;
- attaching said first and second par components to first and second locations of said second vertebra, respectively;
- providing first and second superior facet components configured to replace left and right natural facets of a third vertebra, respectively, and wherein each of said superior facet components comprises an articulating surface;
- attaching said first and second superior facet components to first and second locations of said third vertebra, respectively;

articulately connecting said first and second par articulating surfaces to the articulating surfaces of the inferior and superior facet components, respectively; and wherein each of said inferior facet components comprises an elongated curved body extending along a first axis and said body comprises a first cylindrical shaped end, configured to be attached to a location of said first vertebra and a second cylindrical shaped end comprising said inferior facet articulating surface and extending from said elongated curved body perpendicular to said first axis; and wherein in each of said inferior fact components, said first cylindrically shaped end's axis is oriented perpendicular to said second cylindrical end's axis and perpendicular to said elongated curved body's first axis.

16. The method of claim 15 wherein said connection of said par components to said inferior and superior facet components comprises a constrained articulation mechanism and wherein said constrained articulation mechanism comprises a male articulation component engaging a female articulation component.

\* \* \* \* \*